United States Patent
Drook et al.

(10) Patent No.: US 9,670,444 B1
(45) Date of Patent: *Jun. 6, 2017

(54) ETHANOL PROCESSING FACILITY CAPABLE OF USING A PLURALITY OF DIFFERENT FEEDSTOCKS

(71) Applicant: Central Indiana Ethanol, LLC, Marion, IN (US)

(72) Inventors: Gary Drook, Converse, IN (US); Eric Utterback, Swayzee, IN (US); Ryan H Drook, Indianapolis, IN (US); Randy Baer, Wabash, IN (US); Jeff Harts, Converse, IN (US); Jason Drook, Noblesville, IN (US)

(73) Assignee: Central Indiana Ethanol, LLC, Marion, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/909,129

(22) Filed: Jun. 4, 2013

Related U.S. Application Data

(63) Continuation of application No. 13/848,700, filed on Mar. 21, 2013.
(Continued)

(51) Int. Cl.
*C12M 1/00* (2006.01)
*C12M 1/33* (2006.01)

(52) U.S. Cl.
CPC ............ *C12M 21/12* (2013.01); *C12M 43/02* (2013.01); *C12M 45/02* (2013.01); *C12M 45/03* (2013.01); *C12M 45/04* (2013.01); *C12M 45/20* (2013.01)

(58) Field of Classification Search
CPC ...... C12M 21/12; C12M 45/02; C12M 45/06; C12M 45/20; C12M 43/02; C12P 7/06; C12P 7/08; C12P 7/10; C12P 7/12
(Continued)

(56) References Cited

U.S. PATENT DOCUMENTS 5,135,861 A * 8/1992 Pavilon .......................... 435/162
7,244,597 B2 * 7/2007 Veit et al. ...................... 435/161
(Continued)

*Primary Examiner* — Wiliam H Beisner
(74) *Attorney, Agent, or Firm* — E. Victor Indiano; Indiano & McConnell, LLC

(57) ABSTRACT

An ethanol production facility is provided for processing a plurality of fermentable feedstock materials into an ethanol end product through fermentation and distillation. The facility includes a fermenting stage for converting the plurality of fermentable feedstocks into an alcohol mixture including ethanol and water, and a distillation stage. The distillation stage distills the low concentration alcohol mixture into a high concentration alcohol distillate. A kernel feedstock processing stage is receives and processes a kernel containing feedstock, and includes a receiving station for receiving the kernel containing feedstock. A storage station is provided for storing the kernel based feedstock, and a mill is provided for milling the kernel based feedstock into a flour based feedstock. A conveyor is provided for conveying the milled floor based feedstock to the fermenting stage. A flour feed stock processing stage is operable in parallel with the kernel feedstock processing stage for receiving and processing a flour predominant feedstock. The flour feedstock processing stage includes a storage station for storing the flour for predominant feedstock, and a pneumatic conveyor for conveying the flour to the fermenting stage.

17 Claims, 8 Drawing Sheets

Related U.S. Application Data

(60) Provisional application No. 61/613,974, filed on Mar. 21, 2012.

(58) Field of Classification Search
USPC .................. 435/161–165, 289.1; 44/639
See application file for complete search history.

(56) References Cited

U.S. PATENT DOCUMENTS

| | | | |
|---|---|---|---|
| 2006/0177916 A1* | 8/2006 | Stewart et al. | 435/161 |
| 2010/0071602 A1* | 3/2010 | Hernandez | 110/244 |
| 2010/0196979 A1* | 8/2010 | Birkmire et al. | 435/161 |
| 2010/0203607 A1* | 8/2010 | Medoff et al. | 435/165 |
| 2011/0177558 A1* | 7/2011 | Medoff et al. | 435/72 |

* cited by examiner

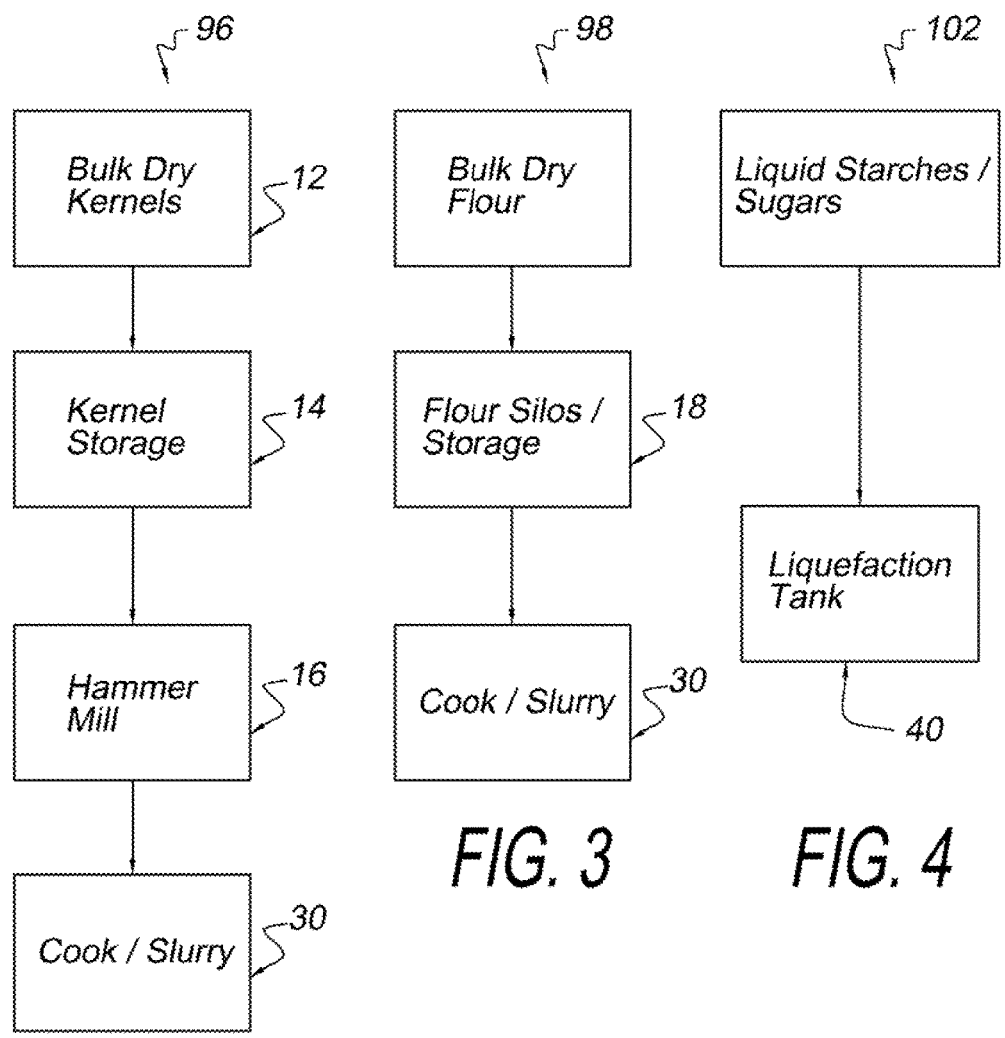

ETHANOL PROCESSING FACILITY CAPABLE OF USING A PLURALITY OF DIFFERENT FEEDSTOCKS

PRIORITY STATEMENT

The instant application claims benefit to Drook and Utterback, U.S. provisional patent application No. 61/613,974, which was filed on 21 Mar. 2012; and is a continuation of, and claims benefit of Drook, Utterback et al Non-Provisional U.S. patent application Ser. No. 13/848,700 filed 21 Mar. 2013; both of which patent Applications are fully incorporated by reference herein.

I. TECHNICAL FIELD OF THE INVENTION

The present invention relates to ethanol producing facilities and more particularly, to ethanol producing facilities that are capable of using a plurality of different feedstocks for fermentation and distillation into a finished ethanol product.

II. BACKGROUND OF THE INVENTION

Grains, yeasts and fruit products have been fermented into ethanol-containing liquids, since biblical time. Additionally, it has been known for centuries that one can take distilled, fermented ethanol-containing products to thereby form a concentrated ethanol- containing product.

Under conventional circumstances, distillation can concentrate the ethanol content in a "wine or beer-like" fermentation product to approximately 95% alcohol. It is difficult to remove the final 5% of water from the ethanol product through distillation because this final 5% water maintains itself in an azeotropic mixture. However, advanced techniques exist for removing this last 5% of water to achieve a final product comprised of almost pure alcohol.

Ethanol can be produced from a variety of feedstocks. Generally, any feedstock having a sugar or starch content can be fermented and ultimately distilled into an ethanol product. Although ethanol has its most famous use in ethanol-containing beverages, a very large amount of ethanol is produced for use as fuel or a chemical reactant for producing other chemicals. Currently, federal regulations encourage the use of ethanol in gasoline fuel products and most gasoline includes about 10% ethanol. Additionally, it has long been known by vehicle manufacturers that vehicle engines can be modified to burn a fuel that is comprised of approximately 100% ethanol. Currently, 100% ethanol fuels are used in major car racing series, such as NASCAR and INDYCAR.

For fuel production, low cost bulk grains having a high starch content are preferably used as the feedstock from which the alcohol is made. In the Midwestern United States, a favorite feedstock is corn, since corn is grown in abundance in the Midwest. In other areas, such as Brazil where sugar is grown in abundance, sugar cane and stalks are used as a preferred feedstock for creating ethanol, whereas wood chips and particles are often used in the timber rich Northwestern U.S.

Most ethanol plants are set up to use a single feedstock for producing ethanol. In the Midwestern states of the United States, the most typical feedstock is corn.

Other sources of feedstock include some types of feedstock that are available on an ongoing basis, and other types of feedstock that are available from time to time. Examples of such regular, ongoing feedstocks include things such as plant waste.

Plant waste can originate from a variety of sources. For example, in a "pasta plant" there will often be some significant amounts of plant waste that occur because of broken pasta, pasta trimmings, floor sweepings and other pasta scraps that somehow do not make it to a finished boxed product. Additionally, corn chip, potato chip and snack product plants also provide a fairly regular source of starch-containing feedstock that can be converted into alcohol. Currently, much of this product is going to animal feed facilities, and can be purchased at relatively low prices.

Another category of potential feedstock can include feedstock that originates from consumer packaged goods. There is a large variety of consumer packaged feedstock that becomes available on the market from time to time. Such feedstocks might include things such as spoiled or out-of-date cake mixes, soft drink products, spoiled breads, potatoes, flours, along with a whole host of other products that have been packaged for either residential or commercial customers, and that are no longer useable by these residential or consumer customers.

One difficulty with dealing with such consumer products relates to their packaging. Along with the cost of purchasing the feedstock, the costs of handling the feedstock in the plant also affects the overall "price of feedstock" and hence, affects the profitability of the use of the feedstock in the ethanol production facility. It can be very difficult, and very labor intensive for one to separate out, for example, the packaging that accompanies a pallet full of spoiled cake mix boxes; or alternately, to open up pallets of spoiled sodas to dump the sodas in the process input, while throwing away the remaining bottles.

Prior to the Applicant's invention, it was difficult, if not impossible for ethanol plants to switch easily between various feedstock types. One thing that made it difficult to switch between feedstocks of different origin, such as switching between a corn flour based feedstock and a wheat flour based feedstock was the different starch content of the various different feedstocks. However, it is even more difficult for a facility to switch between a "flour" feedstock such as a corn flour, and a "kernel" feedstock, such as kernel corn because of the differences in handling required for the different feedstocks.

Currently in the Midwestern United States, the primary feedstock used in ethanol plants is kerneled corn that is bulk delivered to an ethanol plant in either a rail car or a truck. This kerneled corn is then passed through a hammer mill where it is pulverized into a flour and then processed by fermentation and distillation into ethanol. In contrast, a flour feedstock does not behave well in a hammer mill and preferably should not be run through a hammer mill or placed in a holding silo with kerneled feedstock.

Nonetheless, to the extent that flour products are introduced into prior art ethanol plants, the flour feedstocks are passed through a hammer mill, as the hammer mill usually provides the only viable gateway to the cooking and other downstream processing portions of the plant.

Several significant incentives exist for being able to use different feedstocks. In particular, ethanol is often viewed by purchasers, such as oil refining and marketing companies as a "commodity" product. As a commodity product, buyers tend to view ethanol sold from various producers as being fungible, thus leading buyers to purchase their supply of ethanol from the supplier having the lowest prices, or the lowest prices set by the market. Therefore, as with most commodity products, it is not unusual for profit margins for ethanol producers to come under pressure.

One of the most important influencing factors on the final cost of producing ethanol is the cost of the original feedstock which represents over 85% of most ethanol plants' cost of goods sold. Therefore, if one is wedded to the use of a single feedstock, the cost of one's feedstock input will vary along with the current market price of that particular feedstock. If the cost of that particular feedstock rises, and it is difficult for one to maintain consistent feedstock input prices, the cost of producing ethanol at a constant, reasonable cost becomes challenging.

Unfortunately, an ethanol producer is not always in a position wherein he/she can raise the price of its finished ethanol product to reflect the increase in its feedstock prices. One difficulty faced by ethanol producers is that the prices of feedstock corn and finished product ethanol do not always rise or fall together in a lock-step fashion. In some situations, the ultimate buyers of the ethanol output want to pay a constant price for their ethanol, and thus often desire to lock in the ethanol producer into a long term fixed price contract that may not provide the plant flexibility to change its price charged to reflect the changes in prices of the feedstock.

One of the keys to running an ethanol plant at a profit is to purchase its feedstocks at low, competitive, price levels. To a certain extent, one can obtain lower feedstock prices with as single input feedstock grain by timing the purchase of that feedstock at "market valleys". Unfortunately, the lower prices available through strategically timed purchases are often insufficient to achieve overall profitability of the plant or requires excessive market speculation. Further, there are a large number of other feedstock consumers, such as cattle feeding operations, pig farm, chemical plants, food processors and other ethanol producing facilities that are competing for the same low cost feedstocks.

In order to improve profitability, it would be desirable to be able to take advantage of alternate feedstocks, so that one will have a greater variety of feedstocks to choose from and therefore enable the ethanol producer to take advantage of the short term and/or long term opportunities to purchase such feedstocks cost effectively, and thereby boost profitability. For example, the weather during a certain year may be highly unfavorable for corn, but highly favorable for wheat crops, thus causing the price of corn to rise and the price of wheat to fall. In such a case, it would be advantageous to be able to switch from corn to wheat as a feedstock and take advantage of the lower prices available.

Other situations arise on a "spot" basis that enables one to take advantage of ephemeral discounted prices in the market. For example, from time-to-time a train car load of a flour product or sugar product that is destined for a food processor, such as Kellogg's or Pillsbury is determined to be off-spec and/or have an unacceptable contamination issue from a variety of factors including excessive moisture, natural toxins, or insect infestation. A more complete of reasons why feedstocks can become contaminated or distressed and rejected from the human food chain are detailed on Exhibit 1 below.

Exhibit 1

Examples of how material the inventor accepts becomes "waste" include, but are not limited to:
  Food material has passed its expiration date or shelf life
  Foreign material identified in the supply (wood, paper, glass, gravel or other like materials)
  Off-spec product produced (i.e.: rejected as unusable)
  Product has been exposed to air or moisture and spoiled
  Product has turned rancid
  Product is burnt in the manufacturing process
  Product has begun to deteriorate due to mold, bacteria, and/or mildew Rodent infestation:
  Dead rodents found in the product
  Rodents found to have consumed some of the product
  Fecal matter found in the product
  Insect infestation of the food material (beetles, meal worms, ants, maggots, etc.)
  Plant equipment malfunction causing oil or grease to contaminate food material
  Plant metal detectors reject material
  Forklift operators puncture and contaminate bagged material This infestation will often make the car load of flour unacceptable for a human and/or animal food processor. Nonetheless, this rejected feedstock has little to no impact on the suitability of the particular contaminated or distressed feedstock for use in the production of ethanol, and especially ethanol that is ultimately destined for use as a fuel additive to be combusted in a vehicle engine.

As such, the rejected/distressed feedstock may be available to an ethanol producer at a steeply discounted price, relative to the price of corn as a feedstock. Additionally, inefficiencies within the logistics and supply chain of grain products and flour products often causes flour or grains to begin to rot while being stored in silos, bins or rail cars. Although such rotted flours and grains may be unacceptable for use in food products, they are likely still well suited for use in the production of ethanol for use as a motor vehicle fuel blend stock.

Having the ability to switch "on the fly" among various feedstock types with the present invention permits the ethanol producer to take advantage of the ephemeral discounts in the price of these feedstock that arises at irregular times to substantially reduce feedstock prices for a limited quantity of product.

Therefore, it is one object of the present invention to provide an ethanol production facility and a method of producing ethanol, that is able to take advantage of a wide variety of different feedstocks.

III. SUMMARY OF THE INVENTION

In accordance with the present invention, an ethanol production facility is provided for processing a plurality of fermentable feedstock materials into an ethanol end product through fermentation and distillation. The facility comprises a fermenting stage for converting the plurality of fermentable feedstocks into a low concentrate alcohol mixture including ethanol and water, and a distillation stage. The distillation stage distills the low concentration alcohol mixture into a high concentration alcohol distillate. A kernel feedstock processing stage receives and processes a kernel containing feedstock, and includes a receiving station for receiving the kernel containing feedstock. A storage station is provided for storing the kernel based feedstock, and a mill is provided for milling the kernel based feedstock into a flour based feedstock. A conveyor is provided for conveying the milled flour based feedstock to the fermenting stage.

A flour feed stock processing stage is operable in parallel with the kernel feedstock processing stage for receiving and processing a flour predominant feedstock. The flour feedstock processing stage includes a separate storage station for storing the flour predominant feedstock, and a pneumatic conveyor in conveying the flour predominant feedstock to the fermenting stage.

In a preferred embodiment, the ethanol production facility further comprises multiple liquid feedstock processing stages (processors) for receiving and processing a liquid feedstock. The liquid feedstock processing stages include a receiving station and a pump for pumping the liquid feedstock directly into the fermentation stage.

Additionally, the ethanol production facility can further comprise a low moisture feedstock processing stage that is capable of receiving packaged feedstock. The low moisture feedstock processing stage includes a shredder for shredding any packaging that accompanies the low moisture feedstock, a separator for separating shredded packaging front the low moisture feedstock, and a processing stage that includes a roller mill system for milling the low moisture feedstock prior to the low moisture feedstock being conveyed to the fermentation stage.

Additionally, the ethanol processing facility comprises a high moisture feedstock processing stage for processing fermentable feedstocks having a moisture content of greater than about fifteen percent. The high moisture content feedstock processing stage includes as hot water source for placing the high moisture feedstock in an aqueous mixture for transporting the high moisture feedstock containing aqueous mixture to the fermenting stage.

One feature of the present invention is that an ethanol processing facility is provided that is capable of processing and handling a wide variety of feedstocks. This feature has the advantage of giving the ethanol plant operator access to a wider variety of feedstocks than are currently available to ethanol plant operators. Through this enhanced feedstock choice flexibility, the operator can pick and choose among those feedstocks that provide him the opportunity to produce his ethanol end product most profitably.

An additional feature provided by the variety of feedstocks available is that the enhanced flexibility may enable the ethanol facility operator to keep his facility "on-line" during times when the facility operator might otherwise need to shut down due to a scarcity of cost effective feedstocks. Given the high fixed cost nature of an ethanol plant, most processing facilities operate most cost-efficiently by being run continuously, and that shutting down a process due to a lack of feedstocks, often entails significant expense, and can lead to undue equipment failures caused by such a shutdown.

Another feature of the present invention is that it includes a feedstock processing stage that is capable of receiving packaged feedstock. This feature has the advantage of enabling the plant to process feedstocks that while previously available, could previously not be processed cost-effectively. An advantage is gained by being able to process these feedstocks as such feedstocks are often available at quite attractive prices. Through the present invention's ability to enable the user to process these feedstocks, the facility operator can take advantage of these attractively priced feedstocks to help to enhance his profitability.

These and other features and advantages will become apparent to those skilled in the art upon a review of the drawings and detailed description presented below.

IV. BRIEF DESCRIPTION OF DRAWINGS

FIG. 2 is a flow chart providing an overview of the kernel type feedstock processing stage of the present invention;

FIG. 3 is a flow chart showing an overview of the bulk dry flour processing stage;

FIG. 4 is a flow chart showing an overview of the liquid feedstock processing stage;

IV. DETAILED DESCRIPTION OF PREFERRED EMBODIMENT

A. Overview of the Facility

Figure 1:
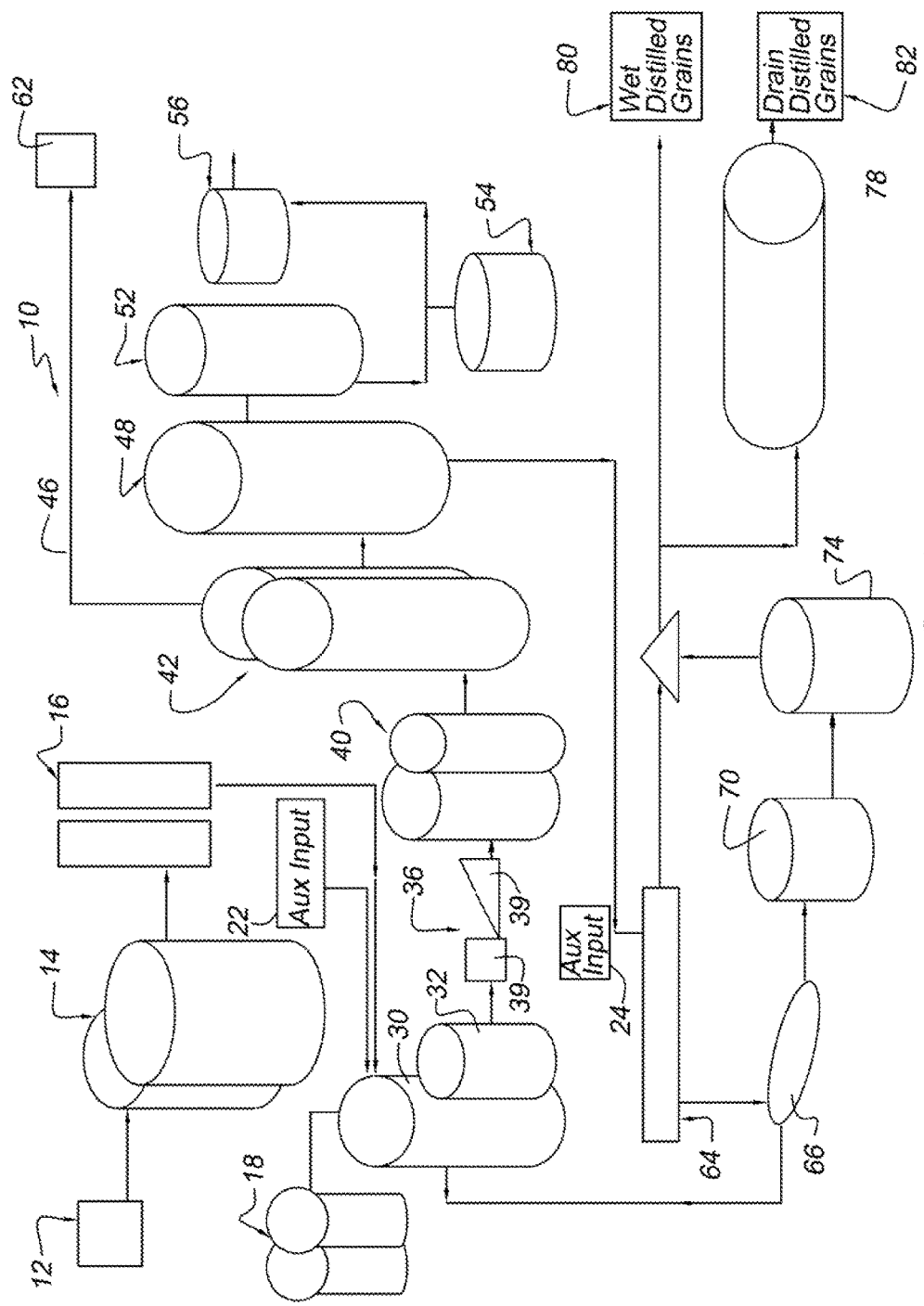
FIG. 1 is a flow chart view illustrating many of the plurality of stages of the ethanol processing facility of the present invention.

An overview of the facility 10 is schematically represented in FIG. 1. Overall, the purpose of the facility 10 is to receive fermentable feedstock products such as grain and grain-origin products and process the fermentable feedstock products into a low concentrate alcohol mixture that includes ethanol and water. The low alcohol mixture (referred to herein as a "beer") is then distilled through a distilling stage to form a high alcohol concentration, alcohol predominant distillate.

After emerging from the distillation stage, the alcohol water mix is then processed through a post-distillation stage wherein the alcohol concentration is raised, and the finished product is stored.

Additionally, byproducts are dealt with and handled in the byproduct processing stage.

In the present invention, there comprises five primary stages. These stages include (1) the pre-fermentation stage; (2) the fermentation stage; (3) the distillation stage; (4) the post-distillation stage; and (5) the byproduct processing stage.

The pre-fermentation stage includes that portion of the process that includes receiving the fermented feedstock, storing the feedstock if necessary, processing the feedstock if necessary to place it in a condition for delivery to the fermentation stage, and then delivering the feedstock to the fermentation stage. As will become more apparent below, this pre-fermentation stage is the primary focus of the present invention, as the present invention relates to a large extent to the various devices and methods that are employed to receive and prepare a plurality of different types of feedstocks so that said plurality of feedstocks may be successfully and cost-effectively processed by the facility in the present invention.

Among the primary components shown at FIG. 1 that relate to the fermentation stage in the facility 10 are the feedstock receiving area 12, the feedstock storage silos and bins 14, a hammer mill 16 for processing kernel-type grain, flour silos 18 for storing flour, a first auxiliary input 22 for receiving and processing other types of fermentable feedstocks and delivering said feedstocks to the fermentation stage, and a second auxiliary input 24 that is capable of delivering processed feedstock products to the liquefaction tanks 40. Unlike the other inputs, the second auxiliary input 24 receives primarily liquid feedstocks, rather than dry, or semi-dry feedstocks as are dealt with the other inputs that deliver their feedstock products to the cooked slurry tanks 30 of the fermentation stage.

The materials that are processed through the facility comprise fermentable feedstock materials that, through a fermentation process, can be converted into an alcohol. Typically, these fermentation products include grains of one sort or another. The term "grains" is used herein in its broadest sense to encompass fermentable products that are capable of producing ethanol when fermented. Grains include such classic grains as corn and wheat, along with other fermentable grain products, and also the processed products of these grains such as meals, flours, and the like, and even consumer end products employing these fermentable feedstocks, such as pastas cake mixes, syrups, soft drinks, sweeteners and the like (see Exhibit 2 for a more complete list such feedstocks).

The fermenting stage of the facility 10 comprises a fermenter that includes as its primary components, cook tanks 30, slurry tanks 32, jet cooker 36, liquefaction tanks 40, and ethanol fermentation tanks 42. The fermentation stage is disposed downstream in the process stream from the pre-fermentation stage.

The fermented "beer" that emerges from the ethanol fermentation tanks 42 comprises a relatively low alcohol concentrate alcohol/water mixture containing between about 2% and 12% alcohol, by volume. The beer is delivered to the distillation stage of the facility 10. The distillation stage comprises a distiller that includes a multi-column distillation column set 46 as its primary component.

After distillation, the ethanol distillate that emerges from the distillation columns has an alcohol content of about 95% ethanol and 5% water. This ethanol predominate distillate is delivered to a post-distillation stage. The primary components of the post-distillation stage include a molecular sieve that helps to raise the ethanol content in the distillate from the approximately 95%/5% ($ETOH-H_2O$) to almost 100% ethanol and no water. The post-distillation treatment stage also includes the denaturant additive tank 54 that adds an additive to the ethanol to make the alcohol non-drinkable. A variety of denaturing agents are known, including gasoline and other similar refined distillates. Finally, an ethanol storage tank 56 is provided where the finished denatured ethanol product is stored until delivery to the customer.

The final post-distillation stage includes the byproduct processing stage. The byproduct processing stage includes two primary paths. The first path includes the path by which carbon dioxide that is given off during the fermentation of ethanol is directed to a carbon dioxide recycling or compression facility 62 wherein the carbon dioxide is converted into dry ice.

The second byproduct is the "bottoms" of the distillation process, that include both solids and liquid materials that remain in a distillation column after the alcohol has been distilled off. The primary components of the byproduct processing stage include a grain recovery centrifuge 64, a liquid recovery tank 66, an evaporation system 80 for evaporating the water off the recovery liquid, and a syrup tank 74 for collecting the syrup that emerges from the evaporation system 80. Solids that are recovered in the process are delivered to a grain drying bin 78. The grain drying bin 78 helps to remove the moisture from the recovered and centrifuged grains before delivering the then dry grains to the dry distilled grain storage area 82. Concurrently, wet distilled grains are delivered to a wet distilled grain storage area 80.

B. Detailed Discussion of the Facility and its Processes From the Fermentation Stage and Downstream Thereof.

As will become more apparent below, the primary focus of the present invention resides in the invention's ability to employ a variety of different feedstocks of different fermentable materials to produce a satisfactory cost-efficiently produced ethanol product.

C. The Fermentation Stage

However, all of the various feedstock processing stages that treat various different feedstock prior to delivery to the fermentation stages ultimately deliver their pre-processed fermentable products to the fermentation stage. These then processed fermentation products are delivered either to the cooks slurry tanks 30, 32 or to the liquefaction tanks 40. Once in the fermentation stage, all of the fermentable materials are treated generally similarly. Therefore, the discussion will begin with the fermentation stage, as it is common generally to all of the various fermentable feedstocks employed. Following is, the new, novel and highly inventive pre -fermentation stages of the present invention shall be discussed. The fermenting stage of the facility 10 comprises a fermenter that includes as its primary components, cook tanks 30, slurry tanks 32, jet cooker 36, liquefaction tanks 40, and ethanol fermentation tanks 42.

The first element within the fermentation stage is a slurry blender 30, that is part of the slurry/cook tanks 30, 32.

The feedstock is fed into the slurry blender 30 where water and an enzyme, alpha amylase are added to the mixture. This mixture of cook water, fermentable material and enzymes is referred to as a slurry mash. The purpose of adding the alpha amylase is to begin breaking down the starch in the fermentable material, and to decrease the viscosity of the mash.

After blending the material thoroughly the slurry blender 30 discharges the slurry mash into the slurry tank 32. The slurry tank 32 has steam injection that helps to bring the temperature of the slurry mash up to approximately 185° F. This temperature is achieved to help the gelatinization of the starch within the mash. Additionally, anhydrous ammonia is added to bring the pH of the mash up to approximately 5.8.

From the slurry tank, the mash is pumped through the jet cooker and more particularly, to the hydro heater 39 of the jet cooker and then into the cook tube 39 of the jet cooker 36. The hydro heater blends the mash with direct steam to raise the temperature of the mash to about 225° F. The mash is brought to this temperature for sterilization, and for shearing the starch molecules.

The mash works through the cook tube and enters the flash vents vessel (not shown). The flash vessel is held under a vacuum and the mash flashes back down to a temperature of 185° F. As the mash leaves the flash vessel, a second dose of alpha amylase is added to the mash before the mash is pumped into the liquefaction tanks 40.

In the liquefaction tanks, the starch in the mash is broken down into complex sugars called dextrose. From the liquefaction tanks 40, the mash is pumped through heat exchangers to reduce the temperature to 95° F. for the fermentation process.

Upon being discharged from the liquefaction tanks 40, and in particular, the heat exchanger thereof, the mash enters into a fermentation tank. Prior to entering this fermentation tank, a yeast slurry from the yeast tank (not shown) is also added to the mash, along with a second enzyme glucoamylase. The glucoamylase is designed to break down the dextrins in the mash into a glucose, the simplest form of sugar, and an ideal food for the yeast.

The yeast slurry is brought in to inoculate the mash with yeast and to begin the fermentation process. The yeast converts the glucose into alcohol and carbon dioxide. This process of converting the glucose into carbon dioxide continues until all of the glucose is suitably converted into alcohol and carbon dioxide.

At the point wherein the mash is fully fermented so that the glucose is contained to alcohol and carbon dioxide, the mixture then contains not only the alcohol and carbon dioxide, but also a sizeable amount of water, and is referred to as a "beer". The carbon dioxide is then vented out of the top of the tank through line 46 into a scrubber. In the scrubber, water is used to wash the carbon dioxide vapor of any alcohol before it is vented off of the tank. Once vented, the carbon dioxide is transferred through line 46 either to a carbon dioxide capture recycle facility or else is vented to atmosphere.

In a preferred embodiment facility of the present invention, a plurality of fermentation tanks are employed, such as three tanks. The reason the multiple tanks are employed is that the fermentation stage is one that requires a significant amount of time to fully convert the glucose within the fermentable feedstocks to ethanol. As such, these fermentation tanks have the potential to create a bottle neck in the process. In order to ensure a constant throughput of materials through the facility 10, enough volume must be provided in the fermentation stage to enable the mash resident in the fermentation tanks to convert into beer in the fermentation stage at a rate that will enable the throughput to remain constant, while providing the mash sufficient time to enable the glucose to be fully converted into alcohol.

In the present invention, the mash is first placed into the first fermentation tank until the first tank is filled up. When filled, the mash is then directed into the second fermentation tank until that tank is filled, and then the third fermentation tank is filled. As the third fermentation tank is being filled, the mash within the first fermentation tank should be fully converted to an alcohol containing beer, and the first tank is then emptied as the third tank is being filled.

Once emptied, the first fermentation tank can be cleaned (if necessary) and then readied for the addition of further mash. After the third fermentation tank is fully filled, the first fermentation tank then begins filling again, while concurrently, the second fermentation tank being prepared for emptying and cleaning.

When the fermenter is finished converting all of the glucose in the feedstock into carbon dioxide and water, the fermented low concentrate alcohol mixture is sent to the distillation stage. The low alcohol content beer will typically have an alcohol content of somewhere in the 2% to 12% alcohol concentration range by volume.

The carbon dioxide that is released through line 46 can be captured so that it will not escape to the atmosphere. The carbon dioxide gas is then vented through lines 46 and is compressed enough so that the gas can be blown to a carbon dioxide liquefaction plant that is preferably located within piping distance of the fermentation tanks, and the ethanol facility. As the carbon dioxide liquefaction plant, the carbon dioxide is compressed further until it is turned into either a liquid product, or further, converted into a solid dry ice product, or to a beverage grade carbon dioxide product. The thus compressed dry ice or beverage grade carbon dioxide can then be used in processes that require dry ice and carbonation, such as the production and serving of carbonated beverages.

D. The Distillation Stage

After emerging from the fermentation stage, the beer is then directed to the distillation stage. The distillation stage comprises a distiller. The primary components of the distiller is a distillation column. In a preferred embodiment, the distillation column includes three distillation columns including (1) a beer column; (2) a rectifier column; and (3) a side stripper column. Beer from the fermentation tanks is pumped into the beer column and alcohol is stripped from the beer by the addition of heat to the bottom of the column via low pressure steam. The alcohol stripped beer residue materials that are now referred to as whole stillage, are pumped from the bottom of the beer column to the whole stillage tank. The whole stillage which comprises the bottoms of the beer column, is then collected and shunted to the centrifuge feedstock recovery, for processing into distiller's grains as will be described in more detail below.

The low proof alcohol in the first column leaves the top of the beer column, in a manner typical of the manner in which a distillate leaves the mixture from which the distillate was distilled. In particular, the distilled alcohol leaves the top of the beer column in a vapor form, and then is directed to the bottom of the rectifier column of the distillation tank. The rectifier column continues to boil the alcohol to bring it up to a 190 proof vapor that leaves the top of the rectifier column. This alcohol is condensed into liquid form by the distillation process and sent to the 190 proof reflux tank, where two-thirds of the condensed alcohol is refluxed back to the top of the rectifier and the rest is pumped into the 190 proof storage tank (not shown).

The boiling, condensation, and refluxing inherent in the distillation column preferably occurs at a rate designed to ensure that the escaped distillate vapor from the top of the column contains only pure alcohol. Preferably, the distillation is conducted quickly enough to ensure good throughput, but slowly enough to ensure that one does not have vaporized water escaping from the fop of the rectifier column, rather than the 190 proof ethanol distillate so desired.

As alluded to earlier, the general limit of water removal that is attainable through a distillation process is approximately 190 proof alcohol, or 95% ethanol/water mixture, since approximately 5% of the water in an alcohol solution tends to remain an alcohol as an azeotrope, which azeotropic water is not removable by distillation.

The bottoms from the rectifiers column is comprised primarily of water with a small amount of alcohol in it. These bottoms are sent into a side stripper column (not shown), where the flash heat from the cook flash tank is used to strip the alcohol from the water, and to add it back to the rectifier column of the distillation stage. The now alcohol-free water from the side stripper is sent back to the cook water stream to be used as processed water in the slurry tank.

The 190 proof alcohol that is distilled out of the top of the rectifier, and reflux tank, is then sent to the post-distillation stage.

E. The Post-Distillation Stage

After the alcohol emerges from the distillation columns, the 190 proof alcohol is then sent to an array of molecular sieves 52. Preferably, three molecular sieves are used, that operate alternately, with one sieve tube being used to strip water from the 190 proof alcohol, the second tube being used in a regenerative mode to regenerate it back so that it has the capability of striping more water from alcohol, with the third tube being used as a standby tube. The 190 proof (95%) alcohol is pumped from the storage tank or the end of the distillation system (as appropriate) into a sieve vaporizer and turned back into vapor form. The 190 proof super-heated vapors enter the top of the molecular sieve bottle 52 and are pushed through the sieve beads that ate contained within the molecular sieve column.

As this high concentrate 190 proof ethanol and water mix is pushed through the molecular sieve tube, it encounters the beads of the molecular sieve. The water molecules become entrained on the beads while the alcohol continues along its path through the sieve tube and falls out the bottom of the sieve bottle as 200 proof vapors. This vapor is then condensed into a 200 proof liquid (essentially pure alcohol) and sent to the 200 proof storage tank 56, where it is blended with the denaturant from denaturant tank 54 to make fuel ethanol suitable for shipment from the facility and delivery to customers.

Additionally, small amounts of the 200 proof vapor is taken from the end of the sieve bottle that is on-line and is used in the bottle that is currently being regenerated. The regeneratively used alcohol helps to strip the water out of the sieve beads and exits out of the top of the bottle in a sieve bottle that is being regenerated. This lower proof alcohol vapor is then sent back to the rectifier column of the distillation stage to be brought up to 190 proof alcohol.

Another aspect of the post-distillation processing of the material in the ethanol processing facility relates to the further treatment of whole stillage, that is drawn out of the bottom of the distillation tank as byproduct. This whole stillage is pumped to centrifuges 64 that are designed to separate solids out of the liquids in the whole stillage by centrifugal force. This centrifugal separation creates two process streams including a solid stream (wet cake) and the liquid stream called thin stillage.

The wet cake is relayed to a set of dryers 78 and the thin stillage is pumped in to an evaporator system 70 to make syrup or otherwise to be used as a back set into the front end of the process.

The evaporator system is comprised of eight tube and shell exchanger-type of evaporators. A tube and shell exchanger is a set of tube that runs the length of the exchanger surrounded by shell or chamber. Thin stillage is pumped to the top of such tubes and gravitates down the length of the tubes while a heating medium such as steam or 200 proof vapor is supplied to the side shell of the exchanger. This causes the thin stillage to boil and evaporate off the excess water that is contained within the stillage.

The water vapor that is produced is from the first four evaporators is used to heat and dry the second four evaporators of the evaporator system array. Finally, the water vapor from the second set of four evaporators is used as low pressure steam to heat the beer column of the distillation stage 48.

The water that is condensed in the second four evaporators ends up being treated in the methonator, and can be reused as processed water. The solids in the thin stillage are raised from approximately four to six percent to around 40 to 45%, making the thin stillage at this point a liquid that is sufficiently viscous to qualify as being called a "syrup".

The syrup can then be collected in syrup tank 74. Part of the syrup stream is diverted for corn oil extraction, where approximately one-third of the corn oil of the syrup is extracted via centrifugal action, when corn feedstock is employed. This extracted corn oil is then sent to a holding tank where it remains until shipment. The remainder of the syrup from the corn oil extraction is then returned to the evaporators to be added back to the syrup stream prior to being sent to a holding tank. The syrup can be sold individually as an animal feed or added to wet cake as it is sent into the dryers. The corn oil can also be sold.

The dryers 78 are used to produce two forms of animal feed, a 10% to 13% moisture product called distiller's dry grains with solubles (DDGS); or a 50% moisture product called modified distillers wet grain with solubles (MD-WGS), which is dried first with syrup added to again make it wet again. Also, 65% moisture product called a distiller's wet grain with solubles (DWGS) is made by bypassing the dryers. In this case, the wet cake coming out of the centrifuges is mixed with syrup and then is conveyed to a wet feed pad.

The distiller's dry grain with solubles (DDGS) is shipped by truck or rail car all over the country, to serve as cattle feed in a wide variety of areas The less valuable modified distillers wet grain with solubles (MDWGS) are shipped by truck usually only within the surrounding area of the facility.

In summary, the outputs from the plant include denatured alcohol that can be sold either alone (E98) or blended with various amounts of fuel by a petroleum refiner, such as Marathon, Shell, or Exxon to create an ethanol-containing fuel, such as E-10 gasoline containing 10% ethanol or a higher volume of ethanol product such as E85. Another output of the product are the wet grains, that can then be sold to farms for use as animal feed. The third primary outputs from the plant comprise syrups and corn oils, that can be sold to appropriate buyers. The final general output from the plant consists of carbon dioxide that can then be compressed into either beverage grade carbon dioxide for use in soft drink production and distribution or dry ice, that can be used as a preservative, and in certain chemical processes.

F. Pre-Fermentation Processing Overview

The various pre-treatment processing stage options available with the present invention are best shown with regard to FIGS. 2-10. As alluded to above, these pre-fermentation processing stages comprise the primary focus of the present invention, as through these pre-fermentation processing stages, the Applicants have found an inventive, novel and surprising way to enable the ethanol processing plant of the present invention to cost -effectively process a significantly wider array of fermentable material feedstocks than was heretofore believed possible, without requiring significant alterations of the processing plant, or else requiring sufficient inefficiencies that would likely cause significant increases in the cost of processing many of the feedstocks. As such, the present invention renders such feedstocks effectively economically eligible for processing in an ethanol processing facility, since the efficiencies achieved by the Applicants make it cost-effective to process these feedstocks while generating a profit for the facility on ethanol produced.

Turning now to FIGS. 2-10, there exist five primary feedstock processing stages that are available via the present invention. These five processing stage pathways receive and treat the incoming feedstocks, and pre-process the incoming feedstock so that the feedstock is suitable for placement into the fermentation stage of the processing facility, at either the cook tank 30, or the liquefaction tank 40 in the process. These five different processing stages are useable in parallel with each other, and are designed to cover five different broad genera of potential feedstock. Each of these five genera includes a variety of species of feedstocks, that ultimately provides for as large variety of potential feedstocks that may be utilized by the plant.

Figure 7:
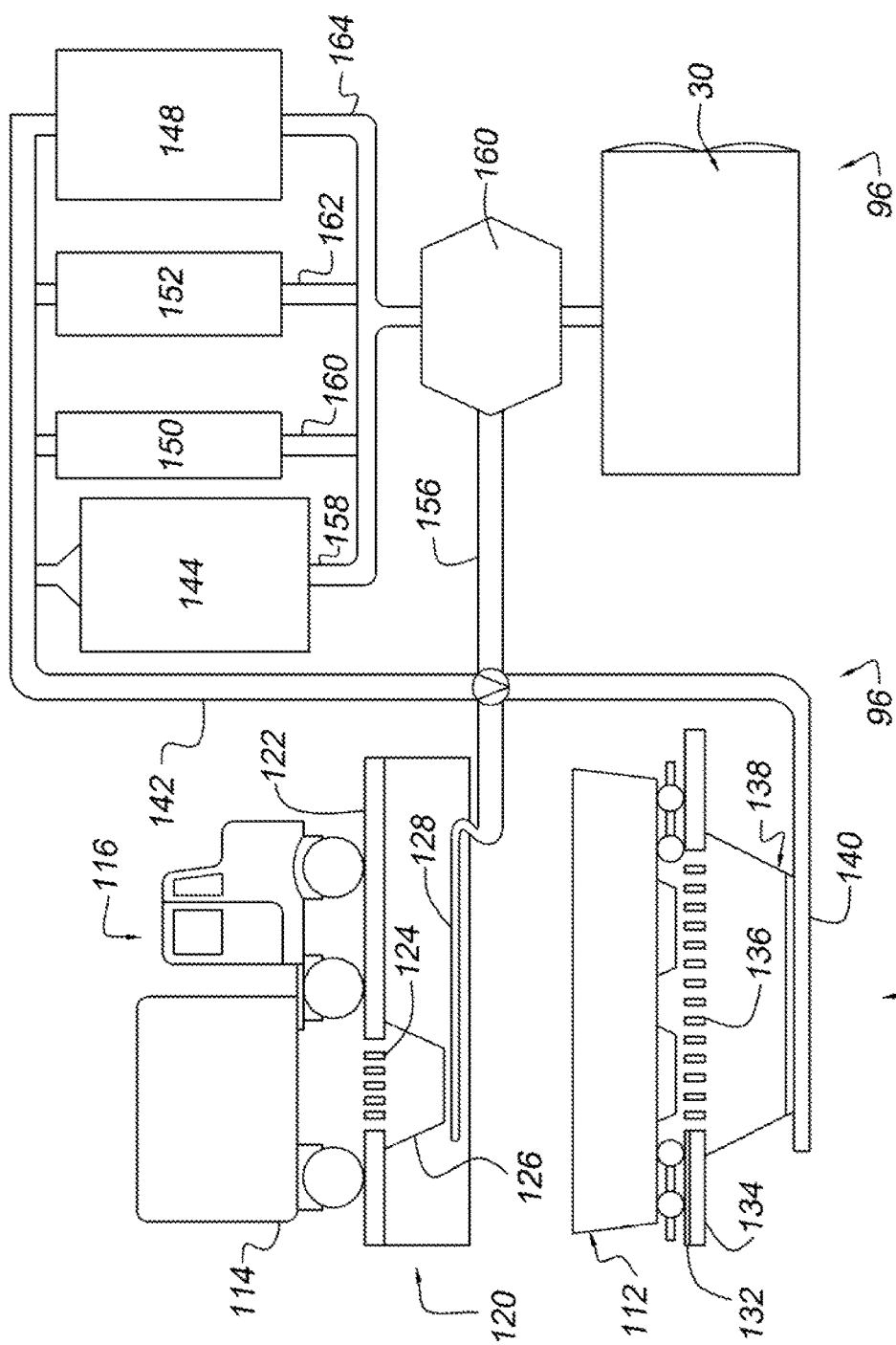
FIG. 7 is a schematic/flowchart showing a more detailed view of the kernel containing feedstock processing stage of the present invention.

The five primary feedstock stages include the kernel feedstock processing stage (kernel feedstock processor) 96 that is shown in brief in FIG. 2 and in detail in FIG. 7. The kernel feedstock processing stage is provided for receiving and processing a kernel-containing feedstock, such as corn that is delivered in a "kernel" form. Currently, the kernel feedstock processing stage 96 comprises the bulk of the feedstock process by the ethanol processing facility 10.

Figure 8:
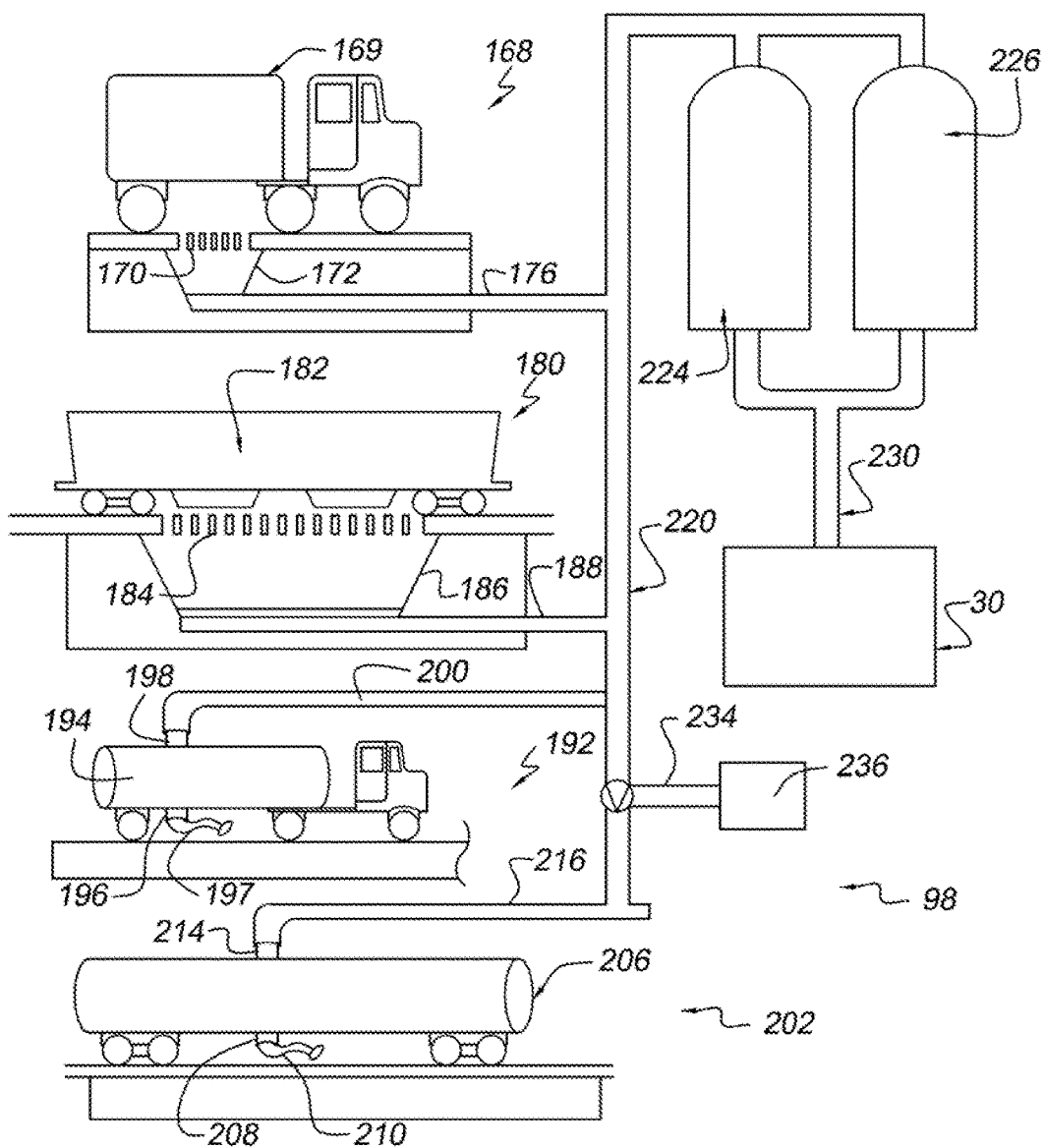
FIG. 8 is a schematic/flowchart showing a more detailed view of the flour predominant feedstock processing stage of the present invention.

The second primary processing stage is the flour feedstock processing stage (flour feedstock processor) 98, that is shown in brief in FIG. 3, and in more detail in FIG. 8. The flour feedstock processing stage 98 is operable in parallel with both the kernel feedback processing stage 96 and all other processing stages of the invention. The flour feedstock processing stage 98 receives and processes a flour predominant feedstock. The flour predominant feedstock differs from a kernel feedstock primarily with respect to the size of particles that comprise the feedstock. Whereas a kernel feedstock comprises kernels of corn, or other product, the flour feedstock is generally more of a powdery smaller particle size substance.

From a practical nature, the kernel-based feedstock requires a hammer mill pre-treatment, so that the kernel type particles of the feedstock are converted into a coarse flour product, before such coarse flour product is fed to the cook slurry 30. On the other hand, usually a flour predominant feedstock does not need to be hammer milled, although certain circumstances exist, wherein it is advantageous to run the flour predominate feedstock through a flour mill prior to placing it in the cook slurry tank 30.

Figure 9:
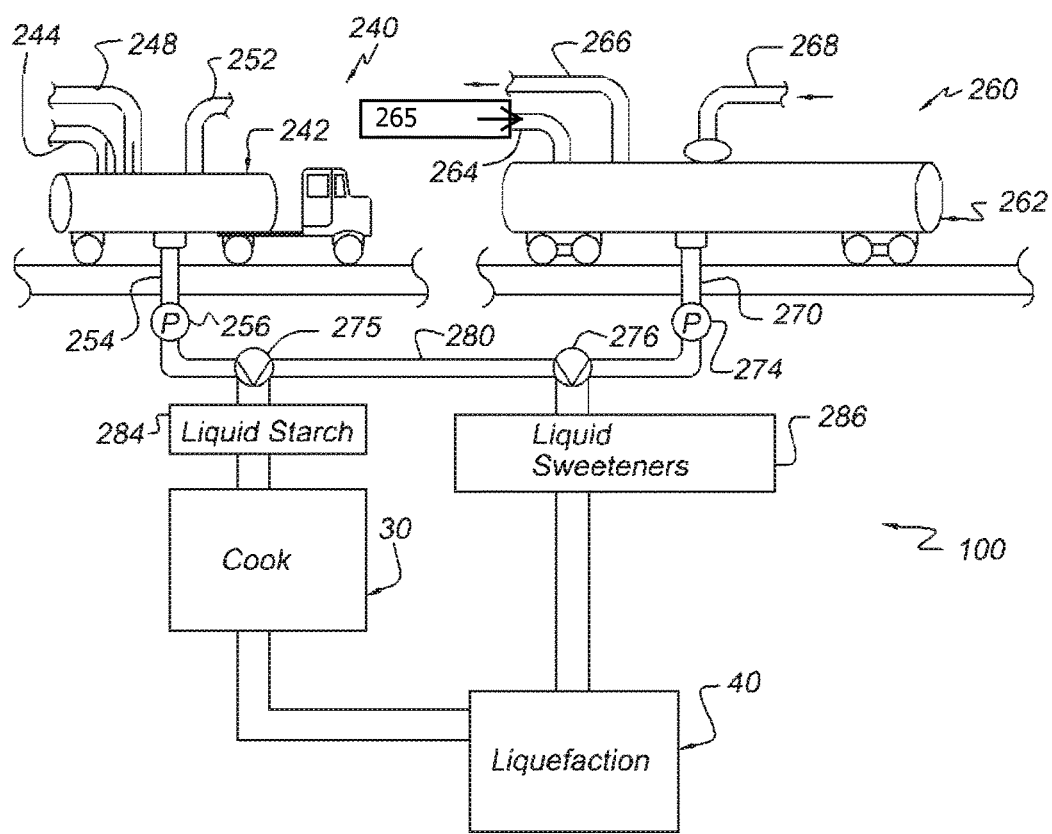
FIG. 9 is a schematic/flowchart showing a more detailed view of the liquid feedstock processing stage of the present invention.

The third primary stream comprises a liquid feedstock processing stage 102 that is shown in brief overview in FIG. 4, and in more detail in FIG. 9. The liquid feedstock processing stage 102 is provided for receiving and processing a liquid feedstock. Examples of liquid feedstock include such things as liquid syrups, liquid starches, liquid sweeteners and the like.

Figures 5, 6:
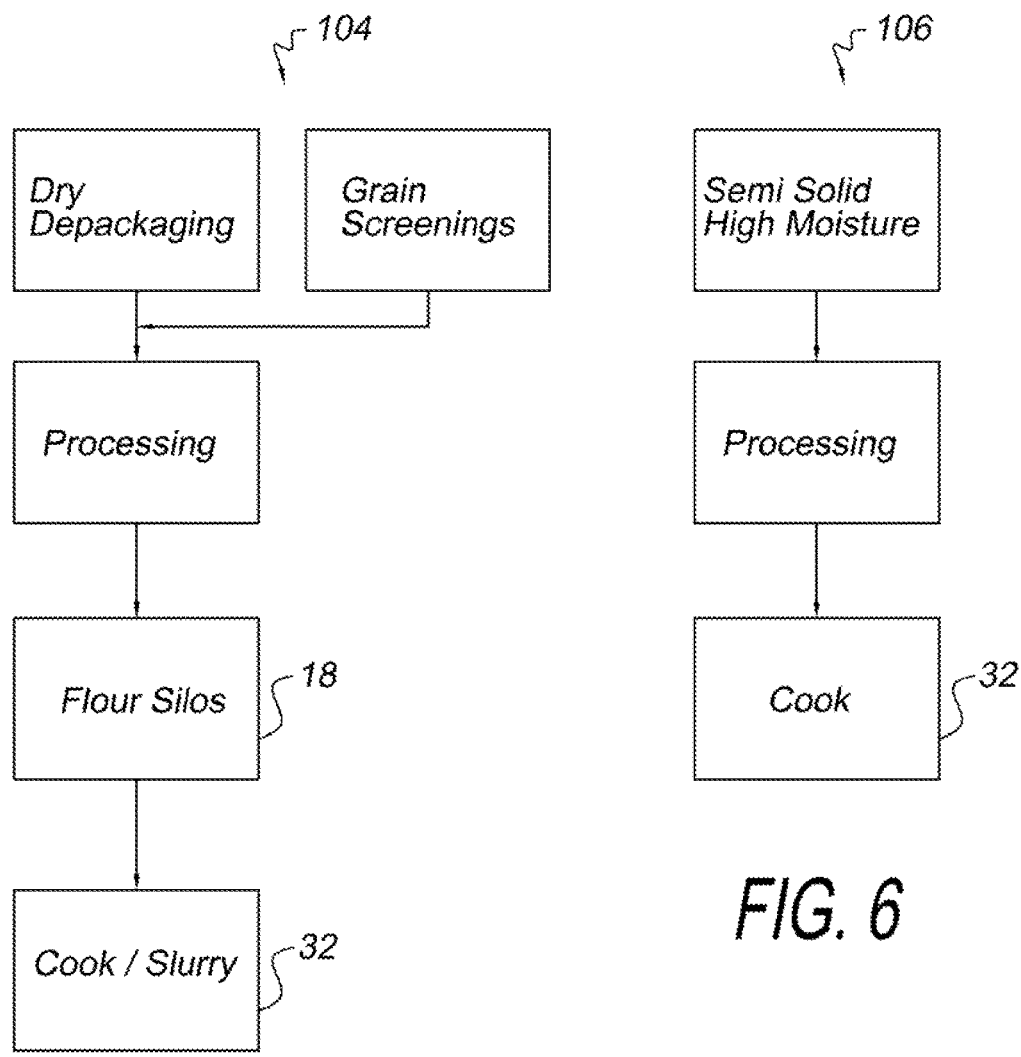
FIG. 5 is a flow chart showing an overview of the low moisture content feedstock processing stage.
FIG. 6 is a flow chart showing an overview of the high moisture content feedstock processing stage.

The fourth feedstock processing stage comprises a low moisture feedstock processing stage 104 that is shown in brief schematically in FIG. 5, and in detail in FIG. 9. The low moisture feedback processing stage of the present invention is capable of receiving packaged feedstock, and is capable of both separating the feedstock from the packaging that contains it, and separating the packaging from the feedstock in a manner that preferably enables the packaged feedstock to be processed in a cost-effective manner. Low moisture feedstock generally consists of feedstock wherein the moisture content is generally at 15% or less.

Figure 10:
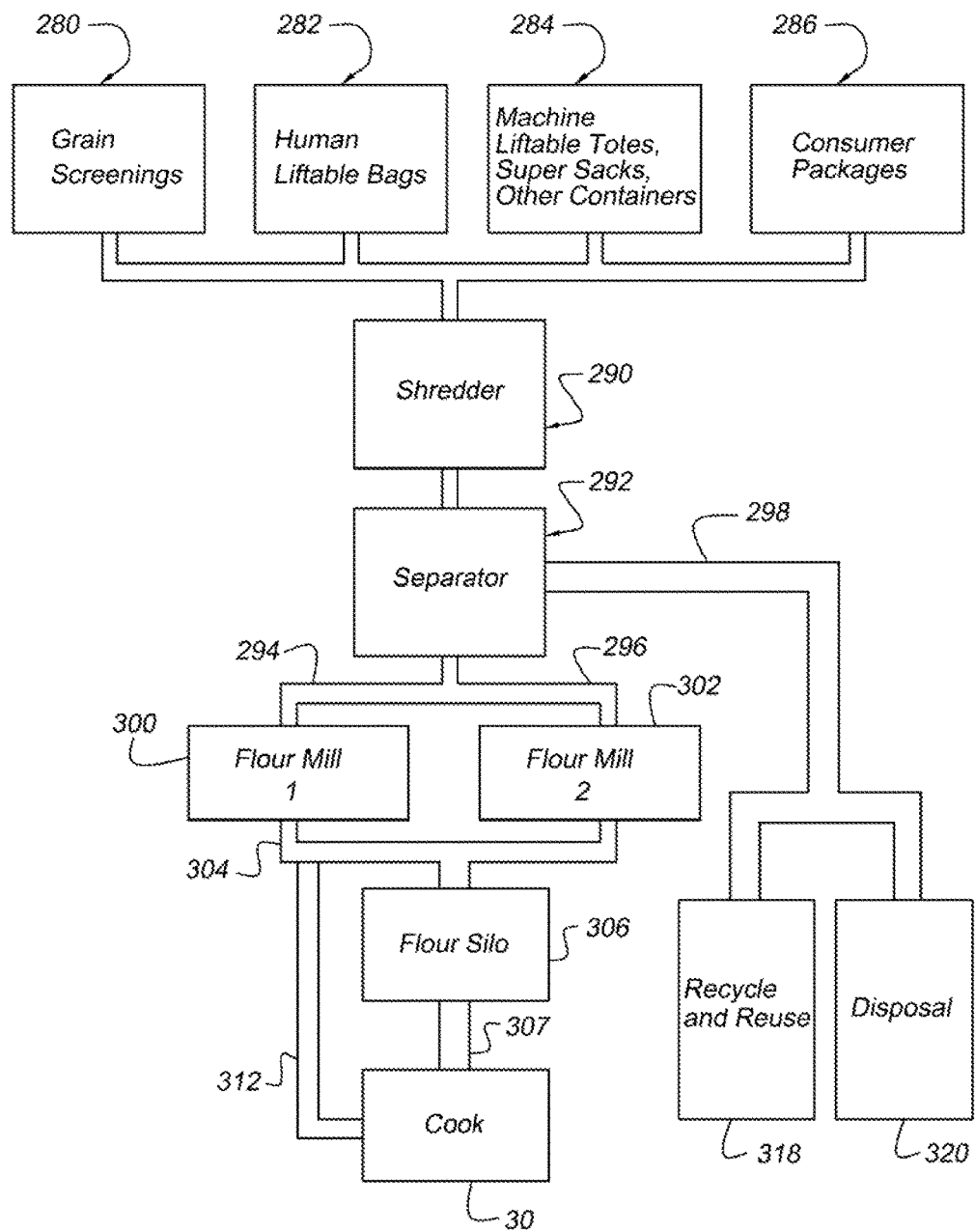
FIG. 10 is a schematic/flowchart showing a more detailed view of the low moisture content feedstock processing stage of the present invention.

The fifth feedstock processing stage of the present invention is shown in brief at FIG. 6 and in detail in FIG. 10. The fifth or semi-solid high moisture content feedstock processing stage 106 has particular utility in dealing with feedstocks having as high moisture content, that, while not liquid, is typically greater than about 15%. Such high moisture feedstocks include things such as icing, bread dough and other semi-moist materials or more volatile dry feedstocks that are more safely handled in an aqueous solution such as raw or refined cane sugar granules.

As stated above, all of the five primary feedstock processing stages are designed to operate in parallel with each other, and with some exceptions, generally independently of each other. To date, it has been found that the primary feedstock stages are capable of cost-effectively processing the following feedstocks.

G. Feedstocks

A wide variety of Feedstocks can be processed by the process of the present invention, with the primary criteria being that the feedstocks be fermentable to produce alcohol; and cost effectively purchased and handled so that the particular feedstock or feedstocks that the user decides to employ can be purchased and processed cost-effectively to enable the facility to profit through the processing and conversion of the particular feedstock or feedstocks chosen into an alcohol end product. Examples of the feedstocks that can be used are presented below as Exhibit 2. As alluded to throughout the application, the particular feedstock(s) chosen is at the discretion of the operator, and there is no requirement that any one feedstock or group of feedstocks be used in the preparation of any particular batch of final product. Depending upon their particle characteristics (flour or kernel); their mode of arrival at the facility (e.g. bulk trailer, bulk rail car, consumer package, human liftable package, machine liftable package consumer package; roll off container, etc; moisture content; and need for further processing, the feedstocks set forth below will assigned to be processed in an appropriate one of the five feedstock processing stages, including (1) the kernel feedstock processing stage; (2) the flour predominant feedstock processing stage 98; (3) the liquid feedstock processing stage 102; (4) the low moisture processing stage 104; and (5) the semi-solid high moisture content feedstock processing stage Examples of these feedstocks are set forth below as Exhibit 2

Exhibit 2

Examples of the plurality of feedstocks, processed across the invention, can include, but are not limited to:

Alcoholic Beverages, including beer, wine, liquor
Baby Food, formula & food
Bakery Goods, including pastries, muffins, rolls & by products
Barley Flour
Breads, all varieties
Candy, all varieties including breakfast bars
Cereals, all varieties
Corn Flour
Corn Screenings Dust
Corn Syrup
Dextrose
Energy Drinks
French Fries
Frozen Sweets, all varieties
Fruits & Fruit juices
Granulated & Powdered Sugar
Hominy
Hominy Feed
Milo Screenings or Flour
Oatmeal
Pasta, all varieties of hard & soft
Popcorn
Popcorn Screenings
Rice & Rice Flours
Snack Foods, including crackers, cookies, chips, dips, & nuts
Soft Drinks, carbonated & un-carbonated
Soups, Sauces, Gravy, & Mixes
Straight & Modified Corn Starch
Sugar Beets
Taco Shells
Waffles
Wheat Screenings Dust
Wheat Flour (Durum, Soft, & Hard)
Wheat Screenings The Feedstock type that are among the most likely to be processed by the kernel feedstock processing stage are bulk kernelled byproducts, such as kernelled corn and other suitable products, many of which are set forth in Exhibit 2. The Feedstock types that are among the most likely to be processed by the flour predominant processing stage include bulk received flour products such as wheat and corn flour and other suitable products, many of which are set forth in Exhibit 2.

The Feedstock type that are among the most likely to be processed by the liquid feedstock processing stage include such things as liquid sweeteners, liquid starches, corn syrups and other suitable bulk received products, many of which are set forth in Exhibit 2.

The type of feedstocks that are well suited for processing by the low moisture processing stage 104 of the present invention include such things as grain screenings, bag feedstock, tote packaged stocks, super sack packaged feedstocks, gaylord packaged feedstocks, consumer packaged feedstocks, bulk box package feedstocks, bulk bin feedstocks, skid box packaged feedstocks, packaged cake mixes, packaged flours, packaged sugars, packaged corn meal mixes, packaged bread and other baking product mixes. pasta sweepings, corn chips and potato chip wastes, and other suitable products, many of which are set forth in Exhibit 2.

Examples of feedstock that can be processed well through the semi-solid high moisture content feedstock processing stage include such things as bread dough, soft drinks, Pop tarts any sugar or carbohydrate-containing drinks, (what else Your attention is now directed to FIGS. 2 and 7 that illustrate the dry bulk kernel processing stage.

H. Bulk Kernel Feedstock Processing Stage

The kernel processing stage 98 includes at least one of a vehicle (e.g. 111, 114) receiving station (e.g. 120, 130), a vehicle unloader (e.g. 124, 128, 136, 138) a kernel feedstock storage container (e.g. 144, 148, 150, 152), and a mill (e.g. 160), Bulk kernel product arrives at the facility 10 traditionally via one of two transport vehicles, either bulk rail or bulk truck. Almost always, the kernels arrive in hopper vehicles such as hopper rail cars 112 or hopper trailers 114 pulled by trucks 116. As fits their name, hopper rail cars 112 and hopper trucks 116 generally include a bulk, tub-like container having a "openable hopper" at its bottom. The hopper can be closed during transport to maintain the material within the bed of the trailer or railcar or opened, to allow material to fall out the bottom of the truck trailer 114 or rail car 112 under the influence of gravity.

In addition to hopper type trailers 114, it is envisioned that occasionally kerneled product will arrive in a dump-type trailer. Examples of rail car type hopper cars, tractor trailer hopper cars and truck dump trailer are readily available by conducting an appropriate search engine search for "truck hopper trailer", "rail car hopper trailer", "railroad hopper car", and "end dump semi-trailer".

As shown in FIG. 7, a truck receiving station 120 is provided for receiving the hopper truck 116 and its hopper trailer 114. The truck receiving station 120 includes a road surface on which the truck can drive. A grate 124 is formed in the road surface 122 that is disposed over a receiving bin 126 that itself is in communication with a conveyor 128. To upload the trailer 114 of kerneled product, the truck driver pulls the truck 116 to position the hopper over the grate 124. The hopper of the trailer 114 is then opened, to allow the kerneled product to fall under the influence of gravity, through the grate 124 and into the receiving bin 126. From the receiving bin, the kerneled product can be moved by conveyor 128 away from the receiving station.

FIG. 7 also shows the presence of a railcar receiving station 130 that includes a rail 132 on which the railcar 112 can ride. A rail bed 134 supports the rail 132 and includes a grate 136 formed therein. The grate 136 is disposed over a receiving bed 138, that itself is in communication with the conveyor 140. In order to unload bulk kernels from the railcar 112, the railcar 112 is moved into position on rail 132 above grate 136. The hopper of the railcar 112 is then opened to allow the kernels to fall, under the influence of gravity, through the grate 136 and into receiving bin 138. The kernels that fall into receiving bin 138 can then be allowed to be conducted by conveyor 140 away from the receiving station.

Kernels that are placed on either of conveyers 128, 140 are normally transported via conveyor 142 to one of four available storage containers, including two storage silos 144, 148, and two storage bins, including first storage bin 150 and second storage bin 152. Alternately, the dry kernels on the conveyors 128, 140 can be shunted through conveyor 156 directly to hammer mill 160. It will also be noted that conveyor systems, such as first 158, second 160, third 162 and fourth 164 conveyors are provided for conveying corn from the respective first 144 and second 148 storage silos, and the first 150 and second 152 storage bins to the hammer mill 160.

The particular choice of whether to use a common conveyor, or four separate conveyors, such as conveyors 158, 164 for transporting bulk kernel corn from the respective storage containers 144, 148 to the hammer mill 160 is largely a question of choice and logistics. It is envisioned that it will be desirable to enable the plant operator to choose the particular storage facility 144, 148 from which to draw feedstock at anyone particular time, and as such, the various corn storage silos and bins 148-152 should be independently accessible. Nonetheless, assuming that they are independently accessible, the conveyor arrangement is largely otherwise dictated by positioning logistics, capacity and the like. It has been found by the Applicants that an auger type conveyor will often work well for conveyors 158-164.

Although typical kernel grains that might pass through the kernel feedstock processing stage 96 are primarily envisioned to be corn type kernels, other kernel products could exist that would be handled through the kernel processing stage. These other kernels include such things as wheat kernels, hominy kernels and barley kernels. Although one could physically process a kernel such as a soybean, or other bean kernel, it is likely that such bean kernels would not be processed through the kernel processing stage, since such products contain a higher protein content than starch content, and as such, are likely to be converted into fuel or oils, such as soybean bio-diesel products, rather than fermented and converted into an alcohol-based fuel product.

In the most preferred embodiment processing facility of the present invention, the storage capacity of the various storage bins exceeds several million bushels of product. Several reasons exist for providing such storage capacity. The first reason is to ensure sufficient inventory of feedstock, since the downstream fermentation, distillation and other processing of the feedstock product works best when it is working continuously on a 24 hour per day, seven day per week basis. Additionally, it is fiscally useful to have the capacity to store large amounts of inventory, to enable the operator to take advantage of favorable price fluctuations, so that the user may buy larger quantities of the feedstock when feedstock prices are low, to thereby avoid purchasing feedstock products when feedstock product prices are high. Additionally, from time to time, short term price advantageous supplies of feedstock material become available that the operator may find desirable to purchase.

As discussed above, the kernel processing stage does provide an option to divert kerneled product from its normal and typical introduction into the storage members 144, 148, 150, 152 and directly into the hammer mill 160.

The Applicants have found it most useful to provide this alternate path directly to the hammer mill 160 for a variety of reasons. For example, it often occurs that the particular kernel feedstock that is being received by the plant in the particular load, or series of loads, has qualities that may cause problems within the kernel silo, if the kernel product was placed in the silos or bins 144, 148, 150, 152 with other kernel products already being stored therein. For example, some kernel products such as corn fines, corn screens, or corn products have qualities that make them unsuitable for placement in a silo or bin 144-152. As such, one may seek to direct such material directly to the hammer mill, and then directly into the fermentation stage 30.

Another example of kernel products that one might not wish to place into the storage silos and bins 148-152 are kernels having an especially high moisture content, such as those that one might receive directly after harvest that have not had a chance to dry. It has been found that such wet kernels have a tendency to clog with the dried kernels and also to begin fermentation within the silo.

Hammer mills have been used for quite some time in grain processing, to shred or crush kernelled grain material into smaller pieces. Essentially, a hammer mill is a steel drum that contains a vertical or horizontal rotating shaft or drum on which hammer mills are mounted. The hammers are free to swing on the ends of the cross, or are fixed to the central rotor. Rotors rotate at a high speed inside the drum while material is fed into a feed hopper. The material is impacted by the hammer mill bars and is thereby shredded and expelled through screens in the drum of the selected size.

I. The Flour Predominant Feedstock Processing Stage

Turning now to FIGS. 3 and 8, the flour feedstock processor 98 will be discussed. The flour predominant feedstock processor 98 is best shown in FIG. 8 as including a hopper truck receiving station 168, a rail hopper car receiving station 180, a pneumatic truck trailer receiving station 192, and a pneumatic railcar receiving station 202. It is believed that the bulk flour that will be processed by the feedstock receiving stations 168, 180, 192, 202 of the flour feedstock processor will primarily be transported to the ethanol facility 10 (and ultimately to the fermenter thereof) through one of these four primary conveyances.

The hopper truck receiving station 168 is generally similar to the hopper truck receiving station 120 employed with the kernel processing stage and is provided for receiving a hopper truck trailer combination 169. The floor of the receiving station 168 includes a grate form 170 formed therein, that is disposed over receiving bin 172. In order to unload its load of flour, the truck 169 pulls into the receiving station to position the hoppers over the grate 170. The hoppers are then opened, to allow the flour to fall under the influence of gravity into the receiving bin.

A difference however in the hopper truck receiving station 168 is that a pneumatic conveyor 176 is provided for pneumatically conveying the flour predominate feedstock to first and second flour storage silos 224, 226. The pneumatic conveyor is very efficient when moving flour.

The rail hopper car receiving station 180 is provided for receiving a railroad hopper car 182 that is filled with a flour predominant feedstock product. The rail hopper car 182 is conveyed via rail to a portion of the rail hopper car receiving station 180 wherein the hoppers of the rail hopper car 182 are positioned over the grate 184, which itself is positioned over a receiving bin 186. By opening the hoppers of the rail hopper car 182, the flour within the rail hopper car can be allowed to fall under the influence of gravity into receiving bin 186. The pneumatic conveyor 188 is similar to pneumatic conveyor 176 is provided for conveying the flour received from the rail hopper car 182 to the first and second flour storage silos 224, 226.

The pneumatic truck trailer receiving station 192 is provided for receiving a pneumatic trailer 194. Pneumatic trailer 194 operates by including an air receiving intake port 196, to which a high pressure air hose 197 can be coupled, for pumping air under high pressure into the interior of the pneumatic truck 194. The pneumatic truck trailer 194 also includes a flour removal port, 198 to which a pneumatic conveyor 200 can be coupled.

High pressure air that is fed into the air receiving port, causes the flour, under the influence of the pressure, to be emptied out of the truck, and moved into the pneumatic conveyor 200, and thence, under the air pressure within the pneumatic conveyor 200, moved ultimately to the flour storage silos 224, 226. Although the pneumatic conveyor 200 is shown as being disposed above the trailer 194, and the air intake receiving port 196 is shown as being disposed below the trailer, it will be appreciated that these positions can be reversed, to enable gravity to enhance the movement of the flour through the pneumatic flour conveyor 200.

The railcar receiving station 202 is generally similar to the truck receiving station, except that it includes a rail, that permits the pneumatic railcar 206 to be conveyed into the railcar receiving station 202. The pneumatic railcar 206 includes an air intake port 208 that can be coupled to a high pressure air hose 210, for permitting high pressure air to be inserted into the interior of the pneumatic railcar 206. A feedstock exit port 214 is coupled to a pneumatic conveyor 216, to enable the feedstock under the pressure of the high pressure air to be conveyed pneumatically to the first and second flour storage silos 224, 226.

A common conveyor 220 can be employed to convey materials from each of the trailer receiving station 168, rail hopper car receiving station 180, pneumatic trailer receiving station 192 and railcar receiving pneumatic station 202 to the first and second flour storage silos. Alternately, a plurality of conveyors can be used. A choice of whether to use a single or plurality of conveyors depends largely upon the volumes of pneumatically conveyed flour that are typically conveyed from each of the four receiving stations 168, 180, 192, 206.

Additionally, a shunt line 234 should be provided to enable kernel containing flour materials, or other materials in need of further processing to be shunted away from the flour receiving silos 224, 226 and to a further processing apparatus, such as either the hammer mills, or flour mills, that can further process the flour received. Flour within the flour mills 224, 226 is removed by an exit conveyer 230, and conveyed pneumatically by the pneumatic conveyer 230, to the cook/slurry container 30, that is at the upstream end of the fermentation of the processing facility 10 of the present invention.

It is important to note that not all flours are created equal. To a miller, there are two primary categories of flour, including food grade flour and other flours. Typically, other flours (non-food grade) command a lower price than food grade flours. The determination of whether a flour is a food grade flour or not, depends on the particular properties of the flour. One feature of the present invention is that it can use the bulk flour handling and processing capabilities of the flour predominate feedstock processing stage to handle flours of all sorts of grades, both food grade and non-food grade.

By having the capability to handle flours of all different grades, from the highest grades to the lowest grades, from food grade to non-food grade, the present invention expands the possibilities of potential feedstocks that are useable in the plant. The greater flexibility of choice of feedstock materials provides a greater potential for profit, since one is able to take advantage of price fluctuations and bargains in the market, when such bargains and price fluctuations occur, and such products become available.

For example, a very high grade of food grade flour may be available to the ethanol processing facility of the present invention because the particular batch has become spoiled and rotten, and is therefore no longer suitable for food grade flour, and is therefore available at a price that is deeply discounted to the price that it would command as a food grade flour product. Similarly, non-food grade flours are often sold in the animal feed market.

Because the profit margins are highly constricted in the animal feed market, and because the general qualities of these non-food grade flours are often significantly lower than the qualities of food grade flours, these non-food grade flours typically sell at substantially lower prices than food grade flours. This substantially lower price at which these non-food grade flours are sold in the feed market makes these products price competitive for an alcohol producer to purchase under certain conditions. Having the ability to process these flours, gives the user access to flours or potential feedstocks from the plant at low cost prices that would otherwise not be available if the user were unable to process these flours.

For example, one could easily envision a condition where there exists a high supply of non-food grade flour stocks, and a rather low supply of feeder animals in need of these low grade flours. At such times, it is likely that the price of the non-food grade flours would drop, since demand is low, thus enabling the Applicants or other users of the present invention, to obtain such non-food grade flour bulk products at a very low and therefore attractive price.

J. Liquid Feedstock Processing Stage

The liquid feedstock processor 100 is best shown with respect to FIG. 9. The primary components or the processor are a vehicle receiving station (e.g. 240, 260), a source of heat, (e.g. steam) for heating hardened liquid feedstock; and a pump (e.g. 274, 256) for pumping the liquid feedstock into the facility. The Vehicle receiving station includes a liquid bulk tank truck receiving station 240 and a liquid bulk railcar receiving station 260. The liquid bulk truck receiving station 240 is designed for receiving a bulk liquid trailer truck 242 of the kind commonly used today. The bulk tank truck can include a double walled tank, having an inner wall and an outer wall. The space between the inner wall and the outer wall comprises a steam jacket, and the actual bulk liquid is placed interiorly of the inner wall. This steam jacket is provided because heat is often required to apply to transported bulk liquids that may have a tendency to either solidify and crystalize (such as sugars and starches), or else, become too viscous and non-flowable, or freeze such as certain bulk chemicals and water-based products that are transported during cooler times of the year.

As such, the liquid bulk tank truck is provided with a steam inlet and valve 244 and a steam outlet valve 248. By running steam within the steam jacket of the trailer, the bulk liquid within the interior tank can be dissolved and made flowable and pumpable as a liquid. Further, the liquid bulk trailer includes a pressure receiving hose inlet 252 into which an air pressure or other pressure can be applied to the tank to help to force out the contents of the interior of the bulk storage tank, and an outlet port and line 254, that is coupled to a pump 256, to help pump liquid feedstocks contained within the bulk liquid feedstock tank trailer 252 out of the trailer.

Similarly, a liquid railcar bulk liquid feedstock containing car 262 is also constructed with a steam jacket to permit coupling to a steam intake hose and port 264 for receiving stream from a steam source 265, and a steam outlet port 266, so that steam can be passed in the steam jacket. The steam so introduced can heat and thereby liquefy either frozen or solidified liquid fermentable material feedstock that is contained within the bulk liquid tank car 262. A pressure inlet port and hose 262 can be coupled to the tank to employ air pressure to help force fluid out the outlet port in pipe 270 of the bulk liquid container car 262.

A pump 274, 256 is provided for facilitating the process. As will be appreciated pumps 256, 274 can be resident on the respective tank trailer 242 and railcar 262, or else, facility resident. The liquid bulk feedstock material that is removed from the tank trailer 242 and railcar 262 is then conveyed via a single pipe 280 or a multiple pipe array to either a liquid starch processing line 284 or a liquid sweetener processing line 286.

Liquid sweeteners can generally be injected directly into the liquefaction stage 40 of the fermentation stage of the processing facility. However, liquid starch is best delivered directly to the cook stage 30 upstream of the liquefaction stage 40 in the processing facility.

Liquid bulk items that comprise the preferred feedstocks of the present invention include such things as corn syrups, sugars, liquid starches and liquid sweeteners. Liquid sweeteners include such things as fructose, dextrose, and sucrose sweeteners, along with high fructose corn syrup.

As discussed above, bulk trailers 242 and bulk railcars 262 often include steam jackets that enable the liquid bulk materials therein to be heated. This heating is important because liquid sweeteners and starches often have a finite shelf life within a tank car 242 or railcar 262. After a period of time, liquid sweeteners or starches start to harden up, such that they are no longer flowable, and can not be pumped.

This inability of the liquid sweeteners and starches can no longer become pumped creates an opportunity for the Applicants and users of the present invention. In particular, when liquid sweeteners harden, they often change chemically sufficiently so that they are no longer acceptable for use as their originally intended product. Although the hardened sweeteners need not be discarded, there is a limited market for these chemically changed sweeteners.

Often this limited market is not large enough to absorb all of the sweetener product that has hardened. Additionally, this limited market for hardened sweeteners is generally willing to pay only a significantly discounted price for the previously hardened, and chemically changed sweeteners when compared to sweeteners that have not been previously hardened and chemically altered.

This limited market and lower price caused by the hardening of the sweeteners can make these hardened sweeteners an attractive feedstock for the present invention, since they can often be purchased inexpensively enough, and converted to alcohol easily enough, so as to be highly profitable.

One feature of the present invention is that the process of the present invention for converting the feedstocks to a fuel alcohol is not adversely affected by the solidification time of a particular sweetener. Therefore, the Applicants can store liquid sweeteners as a hardened product for an extended period of time as is necessary, or as is economically advantageous to suit the user's desire to introduce the hardened liquid sweetener into the ethanol production process of the present invention. This ability to store the hardened sweetener for a long period of time is generally not available to those who wish to employ the hardened sweetener for food grade products. As such, this provides the Applicants with opportunities to acquire supplies of liquid sweetener when they become available, and thereby build up an inventory. By building up a significant inventory of such liquid sweeteners, the Applicants can meter the liquid sweetener into the process at a consistent rate. By enabling the Applicants to introduce the liquid sweetener into the process of the present invention on a consistent basis, management of the facility's processes becomes easier for the Applicants, since the Applicants' need to adjust the process based on differences of intake feedstock is reduced.

In practice, tank cars 262 and tank trailers 242 that include hardened products are kept on the Applicants' facility, until such time as the liquid product contained therein is needed for introduction into the process of the present invention. At that time, the tank car 262 or tank trailer 242 is coupled to a steam jacket line 265 so that the hardened sweetener or other liquid feedstock product contained therein can be re-liquefied. When the liquid feedstock within the tank car 262 or tank trailer 242 is melted (re-liquefied), the liquid feedstock is then introduced into the liquefaction portion of the fermentation stage. Preferably, this introduction is made before the liquid within the tank trailer 242 or railcar 262 has a chance to re-harden, so that energy inputs needed to re-liquefy the feedstock are applied only once to the tank car 262 or tank trailer 242.

K. Low Moisture Feedstock Processing Stage

The next processing stage is best shown in FIG. 10, and relates to a processing stage and apparatus for processing low moisture feedstocks. This low moisture feedstock processing stage 104 is best shown at FIG. 10 and includes the capability of cost-effectively handling packaged feedstocks, such as feedstocks that are packaged in human liftable 20 pound, 50 pound and 100 pound sacks, or consumer sized packaging such as 1 pound boxes of cake mix, and are also contained in other containers such as totes, super sacks, gaylords and the like.

There are four primary input classes for the low moisture processing stage 104. These four classes include grain screenings 280, human liftable material bags of low moisture fermentable feedstock material 282, machine liftable bags of fermentable feedstock materials 284, such as super sacks, gaylords and other consumers; and consumer packaged fermentable feedstock 286.

Consumer packaged goods include such things as consumer packaged flour and pasta type materials. The qualities that differentiate consumer packaged, low moisture goods from consumer packaged high moisture goods relate primarily to moisture content. The low moisture goods that are passed through the low moisture processing stage 104 generally have a moisture content of about fifteen (15%) percent or less. Examples of such low moisture products include things such as dry cake mixes, dry biscuit mixes, dry flour mixes, pasta products, potato chips, crackers, snack goods and the like. In contrast, high moisture products include such consumer packaged goods as Pop-tarts, bread, jelly doughnuts, jams, jellies, some baked goods with fillings, icing, PET bottles filled with soft drinks, sports drinks and the like. These types of consumer packaged goods would likely have a moisture content of fifteen percent or greater (a more extensive list of all feedstock examples, both low and high moisture, are listed on Exhibit 2).

Consumer packaged goods emanate from a variety of sources. Typically, many flour containing consumer products have a limited shelf life and an expiration date. Products that have not sold by the expiration date must often be discarded or otherwise may not be fit for human consumption. Rather than throw such materials away, the instant invention provides a vehicle for re-using these materials, and converting them into a useful ethanol product. Additionally, consumer packaged materials from time to time may become damaged, such as being rotten, becoming water logged, being contained within a fire, becoming subject to some sort of outside food contaminant or the like, that may make the consumer packaged goods unsuitable for human or food purposes.

Other input material classes include those materials that might be contained within totes or super sacks or gaylords, or other types of machine-liftable containers 284. These containers 284 may contain such things as flour received from a flour plant, or pasta sweepings that might be accumulated as waste materials from a pasta plant or pasta waste material such as cut off pasta ends. The differences between consumer packaged goods and machine liftable container goods primarily reside in the packaging in which they arrive, rather than the content or composition of the actual material contained within the package. Additionally, raw materials that are intermediate products are often discarded in a large volume machine liftable container and thus would be handled as such a large container 384 of the present invention.

One of the criteria in order for a product to be run through the low moisture line is that it be conveyable through a pneumatic conveyor, as pneumatic conveyors are provided for transporting the processed feedstock from the separator (pneumatic conveyors 294, 296), and from the flour mill (conveyor 304) to the cook station, or flour silo 300.

The primary difference between the bag class of materials 282 and the totes class of materials 284 relates to the size of the bag. Typically, the bags 292 and the bag class of material are human liftable bags, and may comprise bags that are, for example, 5 pound bags, 20 pound bags and 100 pound bags. Typically, bags this large are used by wholesale and restaurant consumers. In contrast, the totes and super sacks are typically large bulk volumes of materials, that are contained within a container such as totes, super sacks and gaylords that are sufficiently large so that they require machine lifting. These types of materials often originate from fermentable materials processing and production plants.

The final category is grain screenings. Grain screenings are used within the grain screening class 280. The grain screenings 280 are products that are often byproducts of the corn processing industry.

During the processing of corn, the final finished product is often separated from other materials in the intake product. These intake products include things such as corn, grits, damaged corn, corn fines, corn screenings and the like. These "byproducts" are not the primary product that is produced by the corn processing plant or elevator, but rather are considered byproducts or waste products. Most certainly, they are considered second rate products and do not command the prices that the first grade or primary products command.

Because of their second rate or damaged status, and the fact that they command lower prices, they can be purchased less expensively by the Applicants than primary products. Additionally, even though they may be damaged and not considered "primary products", they still do have a very high starch content, and as such, have a significantly good propensity to be converted cost-effectively into an ethanol product.

Typically, these corn fine and grain screenings arrive at the plant in a bulk form in a railcar or hopper or truck. One factor that differentiates fines and screenings from other bulk material received products such as the bulk kernel product and bulk flour product, is that the grain screenings typically require additional processing, such as through the shredder, separator and flour mill, before they can be delivered to the cook slurry. They do not necessarily need to be hammer milled nor should they be sent directly to the flour silo 300.

The materials received in the low moisture processing stage are first directed to a shredder 290. Shredder 290 is an industrial grade shredder and may be the type of shredder that is similar to the one used in a waste water treatment plant, for shredding materials that flow into a waste water treatment plant. A primary purpose of the shredder is to shred the packaging materials, such as any totes, super sacks, gaylords, consumer packaging or man liftable bags, that are introduced into the shredder and that accompany the fermentable material that is processed on the low moisture processing line.

The shredder helps to cost-effectively separate the packaging material from the fermentable material. By cost-effectively separating the packaging material from the fermentable material, the labor costs that were formerly associated with small volume items, such as cake mix packages and flour sacks are reduced, thus making such small volume packages cost-effective to process.

After the material has passed through the shredder, it then passes into the separator 292. The separator 292 is designed to separate the shredded packaging material that accompanies the fermentable material, from the fermentable material. After being shredded, the packaged material can often be separated by mechanical methods, such as screens, blowers and the like, from the fermentable material. Examples of separators that will function from the present invention are available from both the waste water treatment industry and also the waste recycling industry along with the industrial processing industry.

An example of a shredder/separator that will work in connection with the present invention is a shredder/separator that is manufactured by the Jordon Reduction Solutions of Birmingham, Ala. and is sold as the Model No. MS-5028.

Waste materials that are removed by the separator 292 are shunted off into a refuse line 298. Material in the refuse line 298 can be transported to either one or both of a recycle and reuse facility 318, or a disposal facility 320.

Depending upon the desires of the plant operator, a disposal facility 320 can comprise something as simple as a roll off container that is later carted off by a waste disposal company such as Republic Industries. Similarly, the recycle and reuse facility can comprise something as simple as a roll of container that stores the material for recycling and reuse, and that is then carted off by a recycle operator to a recycling plant where the material is further processed. Alternately, if, for example, sufficient similar waste material is generated, the plant operator may have sufficient feedstock of such disposable materials so as to perform some initial processing on the recycled material, such as smashing, crushing, and compacting the recycled material, palletizing the recycled material or alternately, perform an advanced processing operation such as re-melting plastic waste materials and re-pelletizing such waste plastic materials.

Fermentable material that passes through the separator 290, is then forwarded to a flour mill. In the present invention, pneumatic conveyors 294, 296 can forward the fermentable material to a first and second flour mill, 300, 302 that are operated in parallel with each other. The flour mills are provided for grinding the fermentable materials run through the low moisture line to a point where such materials have a flour like consistency.

A pair of flour mills 300, 302 are used in the present invention, as such pair of flour mills both serves to provide a backup to each other if one needs repair and also provides sufficient capacity for the Applicants' plant. It is envisioned that depending upon the throughput of the low moisture processing stage, that a single flour mill might suffice, or alternately, a large bank of five to ten flour mills may be necessary for very large throughput facilities.

After processing by the flour mills, the then milled material is conveyed pneumatically to a flour silo 306 (that may be the same silo as silo 18 of FIG. 1) where the flour material is stored until it is ultimately transferred pneumatically through pneumatic transfer line 306 to the cook tank 330.

Alternately, the material that emerges from the flour mill may be conveyed pneumatically through shunt line 312 directly to the cook station 30. Such shunting would occur for example, if the plant operator believed that the particular material being sent through the flour mill would not necessarily do well in the flour silo. For example, the material may be too moist to make it desirable to place in the flour silo, as it may cause other flour within the silo to clog, or to ferment. Additionally, the particular flour that is passed through the flour mills 300, 302 may be "buggy" or otherwise infested with some material that will not adversely affecting the ethanol production, might be better kept out of contact with the remainder of the material in the silo.

It should also be noted that some small bits of trash may be removed from the discharge of the flour mill 300, 302. Such discharged pieces are likely to be very small in size and can often be caught by passing the flour through a screen having openings large enough to allow the flour to pass easily there through, but small enough to catch particles of paper that may have become entrained in the flour mill.

L. High Moisture Fermentable Material Processing Stage

Figure 11:
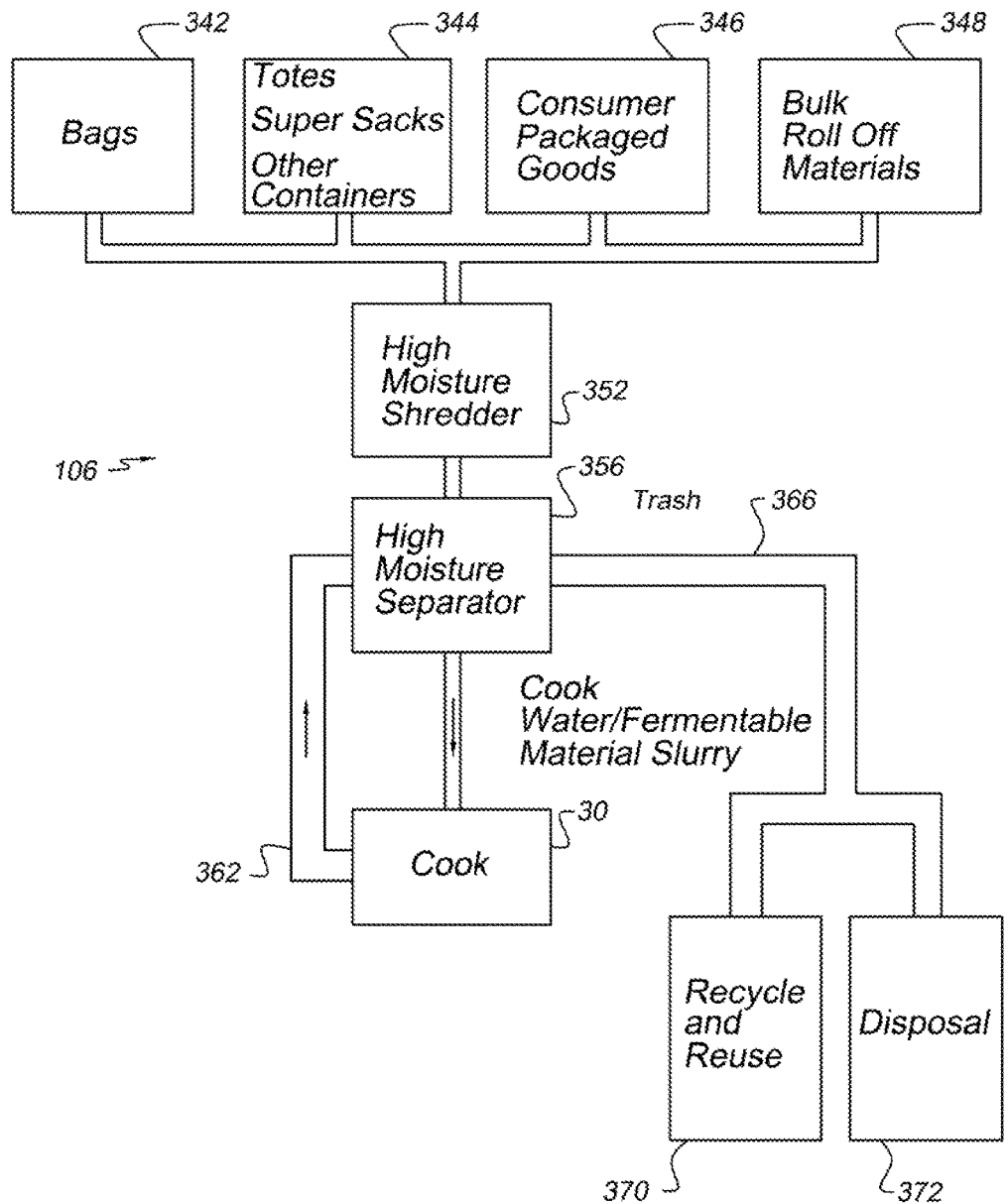
FIG. 11 is a schematic/flowchart showing a detailed view of the high moisture content feedstock processing stage of the present invention.

The high moisture content fermentable feedstock material processor 106 is best shown in connection with FIG. 11, and includes package handline equipment.

There are generally four primary classes of input sources for the high moisture/semi-solid fermentable material feedstock line. These include human liftable bags of feedstock 342, machine liftable, larger containers of feedstock, such as totes, super sacks and other containers 344, consumer packaged goods 346, and bulk roll-off materials.

High moisture semi-solid materials comprise such things as doughy products, breads, food wastes, food rejects, bakery products with high moisture content, such as Pop-tarts, jelly donuts and the like, and other high moisture products that are generally incapable of being conveyed pneumatically through the facility 10 or at best, dissolvable in water, such as sugars that are either comprised of raw or refined sugars. Further, such high moisture materials include such things as cake mixes and other fermentable materials that generally have a moisture content of greater than 15%.

One sort of high moisture material includes corn syrup solids. Corn syrup solids are often found in 20, 50 and 100 pound bags, and provide a large component of the human liftable bag class of materials 342. Modified corn starches are industrial materials that are placed in many of the products where they are used as binding agents. For example, modified corn starches are used by the pharmaceutical companies, paper and packaging industries and are used in adhesives and the like. There is a large amount of these bulk, high moisture products that are currently being bagged. As the moisture content of these starches is often in the 15 to 30% range, these high moisture content materials can easily be contained within a bag since such materials have a consistency of a dough, such as a cookie dough, pizza dough, bread dough or pretzel dough.

One of the problems that was found prior to the Applicants' invention is that it is often not cost-effective to deal with small 20 pound, 50 pound or 100 pound quantities of packaged material when dealing on a scale of material processing typical of the scale of most ethanol production plants. Rather, it is much more convenient and cost-effective to deal with railcar sized containers of materials and truck loads of materials. Prior to the Applicants' invention, it has been difficult to economically and efficiently separate the fermentable materials from the bags in which they are contained, so that the fermentable materials can be entered into the system.

As described below, the Applicants' invention enables such high moisture content material and their accompanying packaging to be dealt with cost-effectively, due to the use of the high moisture content shredder 342 that shreds the packaging and separates it from the fermentable feed stock material and the high moisture separator 356, that helps to separate the accompanying packaged material from the feedstock material, along with the trash disposable feature 366 that removes the separated packaged material, and directs it to either a recycle and reuse facility 370, or disposal facility 372.

Such high moisture content feedstock materials also come in containers that are known as "super sacks", "totes", "gaylords" and the like. These containers are configured very differently than bags and are capable of containing much larger quantities than bags, requiring that such containers be usually moved by machine, such as a fork lift or crane. Typically, totes and super sacks are sized to contain somewhere around 2,000 pounds of material or less, and typically, most sacks, totes and super sacks are capable of carrying between 0.5 tons and 1.0 tons of materials.

Often, super sack-type bags have four loops that can be picked up by a fork lift or other device and hauled over to a pit and emptied. Although these containers are often emptied, they are sometimes just dropped into the shredder or in the tote or super sack is shredded along with the fermentable material contained therein. For example, totes often come in reusable and non-reusable containers. The reusable container would be emptied into the receiving bin. However, a non-reusable container would be placed in the receiving bin and shredded by the shredder downstream of the bin.

Consumer packaging goods that are part of the consumer packaged good class comprise an incredibly wide variety of starch and/or sugar-containing consumer packaged products that might be available on the market. Typically, these consumer packaged goods are packaged in either consumer sizes, or commercial sizes of the type that a cafeteria or restaurant might use. These consumer packaged materials can include things such as high moisture content fermentable material products that come in folded cartons, cardboard cartons, plastic bags, plastic bottles and aluminum cans.

A large potential source of these consumer packaged goods are carbohydrate or fermentable material containing feedstocks, such as soft drinks, spoiled and discarded alcoholic beverages, such as beer and wine and the like. Importantly, many fermentable materials that can be obtained at an appropriate price, are potential feedstock for the process. Such high moisture fermentable materials are appropriate fodder for the high moisture stage of the process.

The final category relates to bulk roll off products. Bulk roll off products include fermentable materials that might originate as a waste from a food plant where they are processed in bulk. For example, a corn chip plant might generate a large amount of waste corn chips and corn chip precursors (flour, etc.) that are removed from the line during a line change over from one end product to another. Additional examples include scrap materials that result from the clean out of machines, floor sweeping, scrap materials that result from trimmings and cut offs of products that are produced in the plant.

It is envisioned that a large number of these products will arrive at the processing facility in roll off containers. A roll off container is a very common product used in the waste industry to contain large volumes of waste. Often, one can see a roll off container at construction sites, and the like. Roll off containers are so called that because they are typically transported by using a winch-line to pull the container onto the bed of a "roll off truck". When the roll off container has reached his desired location, such as a construction site, the container is rolled off the truck and placed at the appropriate site.

In many ways, roll off containers that are useable used with the present invention are identical to these construction site roll off containers, except that preferably, the roll off containers used in connection with the present invention have lids, that both help to prevent the intrusion of foreign matter, and also help to maintain the material within the roll off containers into a more dry state. The ability to preserve dryness is valued as it is likely that the roll off containers that arrive at the processing facility might be stored outside as inventory until such time as the roll off container feedstock can be processed through the facility.

The feedstock material that is run through the high moisture feedstock processing stage 106 is first dumped into a shredder 352. The shredder can be the type of shredder that is used in connection with a waste water treatment plant, or one used in connection with a recycling facility. The shredder 352 grinds everything that enters into it. It not only shreds the container in which the feedstock material is contained, but can also shred the feedstock material.

The shredder should be a high horse power, heavy duty shredder so that it is capable of shredding, at a high throughput rate, such materials as bags, large totes, corrugated boxes, plastic soft drink bottles, aluminum cans and the like. Additionally, the shredder should be able to shred the feedstock material. For example, if a large bulk of dough material is placed within the shredder, the shredder should be able to tear it into smaller pieces.

The then shredded material is fed into the separator 356 that may be formed integrally with the shedder 352. It is within the separator 356 that the cardboard of the cardboard boxes or plastic of the paper bags or totes and cardboard boxes of the consumer packaged materials are separated through shunting line 366 and directed to a disposal facility 372 or recycle and reuse facility 370. The disposal 377 and recycle facility 370 can be generally similar to, or the same as, the reuse and recycle facility and disposal facility disclosed in connection with the low moisture feedstock processing stage.

After exiting the separator 356, the high moisture content materials are pumped into the cook process tank 30. Unfortunately, the often "doughy" nature of the high moisture content products makes their transference to the cook process often difficult, and subject to clogging and the like.

In order to facilitate this transportation, hot cook water is transferred from a cook vat 30 through a return line 362 to the high moisture separator 356. The hot water that emerges from line 362 into the separator 356 is then mixed with the high moisture feedstock material, so that the high moisture content feedstock material may form a flowable, pumpable mixture, that to some extent may comprise a solution, and otherwise, may comprise a suspension or other mixture.

The main thrust of adding the water into the high moisture separator material is that the high moisture content feedstock be sufficiently diluted and flowable so that it can be easily pumped to the cook station 30. The cook water provides not only the water in which the material can dissolve, and that can serve as a carrier, but also the heat that aids in certain materials going into solution into water.

Often, there will not be a downstream storage facility for the material that emerges from the high moisture separator 356, but rather, such materials that emerge from the separator 356 are directed straight to the cooker 30. Although a storage facility might be employed, it is believed at the current time that the high moisture feedstock material is best treated by storing it in its received state, in its bags, totes, super sacks, consumer packaging or bulk roll off containers, and then entering it into the system on an as needed or metered basis.

Having described the invention in detail with reference to certain preferred embodiments, it will he understood that variations and modifications exist within the scope and spirit of the present invention, as defined by the claims presented below.

What is claimed is:

1. An ethanol production facility for processing a plurality of fermentable feedstock materials into an ethanol end product through fermentation and distillation comprising
   a common fermenter for converting the plurality of fermentable feedstocks into an ethanol and water containing mixture, the fermenter including at least one of a cooker, blender, liquefaction tank, and fermentation tank,
   a distiller for distilling the low concentration alcohol mixture into an alcohol predominant distillate wherein the concentration of ethanol in the distillate is greater than in the ethanol and water containing mixture of the fermenting stage, the distiller including a distillation column
   a kernel feedstock processor for receiving and processing a kernel containing feedstock including a receiving station for receiving the kernel containing feedstock, a storage station for storing the kernel based feedstock, a mill for milling the kernel based feedstock into a milled feedstock, and a conveyor for conveying the milled feedstock to the fermenter,
   a flour feedstock processor, operable in parallel with the kernel feedstock processor for receiving and processing a flour predominant feedstock, the flour feedstock processor including a storage station for storing the flour predominant feedstock, and a pneumatic conveyor for conveying the flour predominant feedstock to the fermenter, and
   a low moisture feedstock processor, capable of receiving low moisture feedstock, contained within packaging, the low moisture feedstock processor including equipment for handling packaged low moisture content feedstock, the equipment including a shredder for removing the low moisture feedstock from the packaging in which it is contained and shredding the packaging that accompanies the low moisture feedstock, and a separator for separating shredded packaging from low moisture feedstock, wherein the low moisture feedstock has a moisture content of less than about fifteen percent, and
   a high moisture content feedstock processor for processing packaged high moisture content fermentable feedstock, wherein the high moisture content feedstock processor includes equipment for handling the packaged high moisture content fermentable feedstock for processing the packaging accompanying high moisture content fermentable feedstock, the equipment for handling packaged feedstock including a shredder for shredding any packaging accompanying the high moisture content fermentable feedstock, and a separator for separating the shredded packaging from the high moisture content,
   wherein the milled feedstock from the kernel feedstock processor, the flour predominant feedstock from the flour feedstock processor, the low moisture feedstock from the low moisture feedstock processor and the high moisture content fermentable feedstock from the high moisture feedstock processor are all fed into the common fermenter.

2. The ethanol production facility of claim 1 further comprising a roller mill for milling the separated low moisture feedstock that was removed from its packaging prior to the low moisture feedstock being conveyed to the common fermenter.

3. The ethanol production facility of claim 1 wherein the equipment for handling packaged low moisture feedstock includes equipment for handling each of grain screenings, bagged feedstock, tote packaged feedstock, super sack packaged feedstock, gaylord packaged feedstock, consumer packaged feedstock, bulk box packaged feedstock, bulk bin feedstock, and skid box packaged feedstock.

4. The ethanol production facility of claim 1 wherein the low moisture feedstock processor is configured for processing fermentable products having a fifteen percent or less moisture content including each of corn mix, flour, pasta, dry baby food, dry baby formula, bakery goods, pastries, muffins, rolls, doughnuts, cookies, bakery product by products barley flour, breads, candy, breakfast bars, cereals, corn flour, corn screenings dust, cake mix, dextrose, powdered energy drinks, french fries, sweets, fruits powdered fruit juices, granulated sugars, powdered sugars, hominy, hominy feed, milo screenings, milo flour, oatmeal, hard pasta, popcorn, popcorn screenings, rice & rice flours, snack foods, crackers, cookies, chips, dips, nuts, powdered soft drinks, powdered soups, powdered sauces, powdered gravy, powdered mixes, corn starch, sugar beets, taco shells, waffles, wheat screenings, dust, wheat flour and wheat screenings.

5. The ethanol production facility of claim 1 wherein the high moisture content fermentable feedstock processor is configured for handling high moisture content fermentable feedstock products having a fifteen percent or greater moisture content including each of icing, bread, baby food, baby formula, bakery goods, pastries, muffins, rolls, doughnuts, cookies, bakery product by products barley flour, breads, candy, breakfast bars, cereals, corn flour, corn screenings dust, dextrose, energy drinks, french fries, frozen sweets, fruits, fruit juices, granulated sugars, powdered sugars, hominy, hominy feed, milo screenings, milo flour, oatmeal, hard pasta, popcorn, popcorn screenings, rice, rice flours, snack foods, crackers, cookies, chips, dips, nuts, soft drinks, alcoholic drinks, soups, sauces, gravy, mixes, corn starch, sugar beets, taco shells, waffles wheat screenings dust, wheat flour and wheat screenings.

6. The ethanol production facility of claim 1 further comprising a liquid feedstock processor for receiving and processing a liquid feedstock, the liquid feedstock processor including at least one of a vehicle receiving station, feedstock heater and pump.

7. The ethanol production facility of claim 1 wherein at least one of the low moisture content feedstock processor and the high moisture content feedstock processor includes a roller mill for milling the feedstock prior to the feedstock being conveyed to the fermenter.

8. The ethanol production facility of claim 1 wherein the high moisture content feedstock processor includes equipment for processing high moisture content fermentable feedstock having a moisture content of about fifteen percent or greater, the equipment including a hot water source capable of delivering hot water to the high moisture content fermentable feedstock for placing the high moisture content fermentable feedstock in an aqueous mixture for flowably transporting the high moisture content fermentable feedstock to the common fermenter.

9. The ethanol production facility of claim 8 wherein the fermenter includes the cooker wherein water is heated for heating the high moisture content fermentable feedstock, and wherein the high moisture content fermentable feedstock includes a liquid transport line for transporting water heated in the cooker to the high moisture content feedstock processor for use as the hot water source.

10. An ethanol production facility for processing a plurality of either or both of sugar and starch based fermentable feedstock materials into an ethanol end product through fermentation and distillation comprising
    a common fermenter for converting the plurality of fermentable feedstocks into an ethanol and water containing mixture, the fermenter including at least one of a cooker, blender, liquefaction tank, and fermentation tank,
    a distiller for distilling the low concentration alcohol mixture into an alcohol predominant distillate wherein the concentration of ethanol in the distillate is greater than in the ethanol and water containing mixture of the fermenting stage, the distiller including a distillation column
    a kernel feedstock processor for receiving and processing a kernel containing feedstock including a receiving station for receiving the kernel containing feedstock, a storage station for storing the kernel based feedstock, a mill for milling the kernel based feedstock into a milled feedstock, and a conveyor for conveying the milled feedstock to the fermenter,
    a flour feedstock processor, operable in parallel with the kernel feedstock processor for receiving and processing a flour predominant feedstock, the flour processor including a storage station for storing the flour predominant feedstock, and a pneumatic conveyor for conveying the flour predominant feedstock to the fermenter, and
    a low moisture feedstock processor, capable of receiving low moisture feedstock, contained within packaging and having a moisture content of less than about fifteen percent, the low moisture feedstock processor including equipment for handling packaged low moisture content feedstock, the equipment including a shredder for removing the low moisture feedstock from the packaging in which it is contained and shredding the packaging that accompanies the low moisture feedstock, and a separator for separating shredded packaging from low moisture feedstock, and
    a high moisture content feedstock processor for processing non-flowable high moisture content fermentable feedstocks having a moisture content of about fifteen percent or greater, the high moisture content feedstock processor including a hot water source capable of delivering hot water to the high moisture content fermentable feedstock for placing the high moisture content fermentable feedstock in a flowable aqueous mixture for transporting the high moisture content fermentable feedstock containing aqueous mixture to the fermenter by flowing to the fermenter
    wherein the milled feedstock from the kernel feedstock processor, the flour predominant feedstock from the flour feedstock processor, the low moisture feedstock from the low moisture feedstock processor and the high moisture content fermentable feedstock from the high moisture feedstock processor are all fed into the common fermenter.

11. The ethanol production facility of claim 10 wherein the fermenter includes the cooker where water is heated for heating the high moisture content fermentable feedstock, wherein the high moisture content feedstock processor includes a liquid transport line for transporting water heated in the cooker to the high moisture content processor for serving as the hot water source.

12. The ethanol production facility of claim 10 further comprising a high moisture content feedstock processor for processing packaged high moisture content fermentable feedstock, wherein the high moisture content feedstock processor includes equipment for handling the packaged high moisture content fermentable feedstock for processing the packaging accompanying high moisture content fermentable feedstock, the equipment for handling packaged feedstock including a shredder for shredding any packaging accompanying the high moisture content fermentable feedstock, and a separator for separating the shredded packaging from the high moisture content fermentable feedstock.

13. The ethanol production facility of claim 12 wherein the high moisture content feedstock processor includes a roller mill for milling the high moisture content fermentable feedstock prior to the high moisture content fermentable feedstock being conveyed to the common fermenter.

14. The ethanol production facility of claim 12 wherein the high moisture content feedstock processor includes a transport line for transporting separated packaging materials to one of a recycling facility and a disposal facility.

15. The ethanol production facility of claim 14 wherein the fermenter includes the cooker wherein water is heated for heating the high moisture content fermentable feedstock, wherein the high moisture feedstock processor includes a liquid transport line for transporting water heated in the cooker for providing the hot water source.

16. The ethanol production facility of claim 10, further comprising a high moisture feedstock processor including equipment for handling packaged feedstock for processing high moisture content fermentable feedstock having a moisture content of about fifteen percent or greater.

17. An ethanol production facility for processing a plurality of either or both of sugar and starch based fermentable feedstock materials into an ethanol end product through fermentation and distillation comprising:
    a common fermenter for converting the plurality of fermentable feedstocks into an ethanol and water containing mixture, the fermenter including at least one of a cooker, blender, liquefaction tank, and fermentation tank, a distiller for distilling the low concentration alcohol mixture into an alcohol predominant distillate wherein the concentration of ethanol in the distillate is greater than in the ethanol and water containing mixture in the fermenter, the distiller including a distillation column a kernel feedstock processor for receiving and processing a kernel containing feedstock including a receiving station for receiving the kernel containing feedstock, a storage station for storing the kernel containing feedstock, a mill for milling the kernel containing feedstock into a milled feedstock, and a conveyor for conveying the milled feedstock to the fermenter, a flour feedstock processor, operable in parallel with the kernel feedstock processor for receiving and processing a flour predominant feedstock, the flour feedstock processor including a storage station for storing the flour predominant feedstock, and a pneumatic conveyor for conveying the flour predominant feedstock to the fermenter;

a low moisture feedstock processor, capable of receiving packaged low moisture feedstock, the low moisture feedstock processor including a shredder for shredding any packaging that accompanies the low moisture feedstock, and a separator for separating shredded packaging from low moisture feedstock, wherein the low moisture feedstock has a moisture content of less than about fifteen percent; and a liquid feedstock processor for processing liquifiable fermentable feedstocks that are in one of a liquid state and a state where they can become liquid upon the addition of a liquid, and which are contained in bulk within a delivery vehicle, the liquid feedstock processor including a steam source capable of delivering steam to the delivery vehicle for placing the liquid feedstock in a flowable liquid state for flowably transporting the liquifiable fermentable feedstock to the fermenter, wherein the milled feedstock from the kernel feedstock processor, the flour predominant feedstock from the flour feedstock processor, the low moisture feedstock from the low moisture feedstock processor and the liquefiable fermentable feedstock from the liquid feedstock processor are all fed into the common fermenter.

* * * * *